United States Patent
Tesar

(10) Patent No.: US 10,918,455 B2
(45) Date of Patent: Feb. 16, 2021

(54) VARIABLE LIGHT SOURCE

(71) Applicant: CamPlex, Inc., Germantown, TN (US)

(72) Inventor: John Tesar, Tucson, AZ (US)

(73) Assignee: CamPlex, Inc., Germantown, TN (US)

( * ) Notice: Subject to any disclaimer, the term of this patent is extended or adjusted under 35 U.S.C. 154(b) by 0 days.

(21) Appl. No.: 15/973,433

(22) Filed: May 7, 2018

(65) Prior Publication Data

US 2018/0318033 A1 Nov. 8, 2018

Related U.S. Application Data

(60) Provisional application No. 62/503,262, filed on May 8, 2017, provisional application No. 62/517,089, filed on Jun. 8, 2017.

(51) Int. Cl.
| | | |
|---|---|---|
| *A61B 90/30* | (2016.01) | |
| *F21V 9/20* | (2018.01) | |

(Continued)

(52) U.S. Cl.
CPC .............. *A61B 90/30* (2016.02); *F21V 9/20* (2018.02); *F21V 9/40* (2018.02); *F21V 23/003* (2013.01); *G02B 5/28* (2013.01); *G02B 6/0006* (2013.01); *G02B 6/0008* (2013.01); *G02B 6/06* (2013.01); *G02B 6/264* (2013.01); *G02B 6/32* (2013.01);

(Continued)

(58) Field of Classification Search
CPC ............ A61B 2090/306; G02B 6/0006; G02B 6/0008; G02B 6/264; F21V 9/20
See application file for complete search history.

(56) References Cited

U.S. PATENT DOCUMENTS

| 497,064 A | 5/1893 | Van Meter |
|---|---|---|
| 2,826,114 A | 3/1958 | Bryan |

(Continued)

FOREIGN PATENT DOCUMENTS

| CN | 2336380 Y | 9/1999 |
|---|---|---|
| CN | 101518438 | 9/2009 |

(Continued)

OTHER PUBLICATIONS

Aesculap Inc.; Aesculap Neurosurgery Pneumatic Kerrison; http://www.aesculapusa.com/assets/base/doc/doc763-pneumatic_kerrison_brochure.pdf; 2008; in 12 pages.

(Continued)

*Primary Examiner* — Joseph L Williams
*Assistant Examiner* — Jacob R Stern
(74) *Attorney, Agent, or Firm* — Knobbe, Martens, Olson & Bear, LLP

(57) ABSTRACT

A light source includes features configured to compensate for discontinuous solid state sources. The light source can produce a wide color gamut in display, and improved color rendering of tissue under observation by phosphor gap filling with colored LEDs. The light source can include provisions to depart from a white light spectrum to heighten differences in anatomical features or functions. The light source can include provisions to introduce narrow-band solid-state sources for producing false-color and pseudo-color images, with variable color rendering to change the power spectral distribution and to compensate for fiber optic length and fiber optic diameter tip sensing.

13 Claims, 13 Drawing Sheets

(51) Int. Cl.

| | | |
|---|---|---|
| *F21V 23/00* | (2015.01) | |
| *G02B 6/32* | (2006.01) | |
| *F21V 8/00* | (2006.01) | |
| *F21V 9/40* | (2018.01) | |
| *G02B 6/26* | (2006.01) | |
| *G02B 6/06* | (2006.01) | |
| *G02B 5/28* | (2006.01) | |
| *F21Y 115/10* | (2016.01) | |
| *F21Y 115/30* | (2016.01) | |
| *A61B 90/00* | (2016.01) | |

(52) U.S. Cl.
  CPC ........ *G02B 6/325* (2013.01); *A61B 2090/304* (2016.02); *A61B 2090/306* (2016.02); *A61B 2090/309* (2016.02); *A61B 2090/371* (2016.02); *F21Y 2115/10* (2016.08); *F21Y 2115/30* (2016.08)

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A | 7/1983 | Schoolman |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,718,106 A | 1/1988 | Weinblatt |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,986,622 A | 1/1991 | Martinez |
| 4,989,452 A | 2/1991 | Toon et al. |
| 5,016,098 A | 5/1991 | Cooper et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda et al. |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A | 2/1997 | Miyagi |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A | 11/1998 | Kitajima |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,217,188 B1 | 4/2001 | Wainwright et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,340,363 B1 | 1/2002 | Bolger et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 | 1/2003 | Taylor et al. |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 | 7/2003 | Alfano et al. |
| 6,589,168 B2 | 7/2003 | Thompson |
| 6,618,207 B2 | 9/2003 | Lei |
| 6,626,445 B2 | 9/2003 | Murphy et al. |
| 6,633,328 B1 | 10/2003 | Byrd et al. |
| 6,635,010 B1 | 10/2003 | Lederer |
| 6,636,254 B1 | 10/2003 | Onishi et al. |
| 6,661,571 B1 | 12/2003 | Shioda et al. |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,817,975 B1 | 11/2004 | Farr et al. |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |

(56) References Cited

U.S. PATENT DOCUMENTS

| | | |
|---|---|---|
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,621,868 B2 | 11/2009 | Breidenthal et al. |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover et al. |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey et al. |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,351,434 B1 | 1/2013 | Fukuda et al. |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearman et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph |
| 8,482,606 B2 | 7/2013 | Razzaque |
| 8,498,695 B2 | 7/2013 | Westwick et al. |
| 8,521,331 B2 | 8/2013 | Itkowitz |
| 8,702,592 B2 | 4/2014 | Langlois et al. |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 9,936,863 B2 | 4/2018 | Tesar |
| 10,022,041 B2 | 7/2018 | Charles et al. |
| 10,028,651 B2 | 7/2018 | Tesar |
| 10,231,607 B2 | 3/2019 | Charles et al. |
| 10,555,728 B2 | 2/2020 | Charles et al. |
| 10,568,499 B2 | 2/2020 | Tesar |
| 10,702,353 B2 | 7/2020 | Tesar |
| 2001/0055062 A1 | 12/2001 | Shioda et al. |
| 2002/0013514 A1 | 1/2002 | Brau |
| 2002/0049367 A1 | 4/2002 | Irion et al. |
| 2002/0065461 A1 | 5/2002 | Cosman |
| 2002/0082498 A1 | 6/2002 | Wendt et al. |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0102819 A1* | 6/2003 | Min ............... B60Q 1/2607 315/291 |
| 2003/0103191 A1 | 6/2003 | Staurenghi et al. |
| 2003/0142204 A1 | 7/2003 | Rus et al. |
| 2003/0147254 A1* | 8/2003 | Yoneda ............... G01B 11/00 362/551 |
| 2004/0017607 A1 | 1/2004 | Hauger et al. |
| 2004/0027652 A1* | 2/2004 | Erdogan ............ G01J 3/4406 359/359 |
| 2004/0036962 A1 | 2/2004 | Brunner et al. |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0031192 A1 | 2/2005 | Sieckmann |
| 2005/0033117 A1 | 2/2005 | Ozaki et al. |
| 2005/0052527 A1 | 3/2005 | Remy et al. |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0171551 A1 | 8/2005 | Sukovich et al. |
| 2005/0215866 A1 | 9/2005 | Kim |
| 2005/0228231 A1 | 10/2005 | MacKinnon et al. |
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |

(56) References Cited

U.S. PATENT DOCUMENTS

| | | |
|---|---|---|
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0038080 A1 | 2/2007 | Salisbury, Jr. et al. |
| 2007/0086205 A1 | 4/2007 | Krupa et al. |
| 2007/0129608 A1 | 6/2007 | Sandhu |
| 2007/0129719 A1 | 6/2007 | Kendale et al. |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0094583 A1 | 4/2008 | Williams et al. |
| 2008/0096165 A1 | 4/2008 | Virnicchi et al. |
| 2008/0097467 A1 | 4/2008 | Gruber et al. |
| 2008/0123183 A1 | 5/2008 | Awdeh |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0269730 A1 | 10/2008 | Dotson |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0310181 A1* | 12/2008 | Gurevich ............ G02B 6/0006 362/554 |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0052059 A1 | 2/2009 | Lin |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1 | 7/2009 | Nakamura |
| 2009/0190371 A1 | 7/2009 | Root et al. |
| 2009/0209826 A1 | 8/2009 | Sanders et al. |
| 2009/0238442 A1 | 9/2009 | Upham et al. |
| 2009/0244259 A1 | 10/2009 | Kojima et al. |
| 2009/0245600 A1 | 10/2009 | Hoffman et al. |
| 2009/0248036 A1 | 10/2009 | Hoffman et al. |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0081919 A1 | 4/2010 | Hyde et al. |
| 2010/0107118 A1 | 4/2010 | Pearce |
| 2010/0128350 A1 | 5/2010 | Findlay et al. |
| 2010/0161129 A1 | 6/2010 | Costa et al. |
| 2010/0168520 A1 | 7/2010 | Poll et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1 | 9/2010 | Luley, III et al. |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0042452 A1 | 2/2011 | Cormack |
| 2011/0046439 A1 | 2/2011 | Pamnani et al. |
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0115891 A1 | 5/2011 | Trusty |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |
| 2012/0040305 A1 | 2/2012 | Karazivan et al. |
| 2012/0041272 A1 | 2/2012 | Dietze, Jr. et al. |
| 2012/0041534 A1 | 2/2012 | Clerc et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0089093 A1 | 4/2012 | Trusty |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157775 A1 | 6/2012 | Yamaguchi |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |
| 2012/0320102 A1 | 12/2012 | Jorgensen |
| 2012/0330129 A1 | 12/2012 | Awdeh |
| 2013/0012770 A1 | 1/2013 | Su |
| 2013/0027516 A1 | 1/2013 | Hart et al. |
| 2013/0041226 A1 | 2/2013 | McDowall |
| 2013/0041368 A1 | 2/2013 | Cunningham et al. |
| 2013/0060095 A1 | 3/2013 | Bouquet |
| 2013/0066304 A1 | 3/2013 | Belson et al. |
| 2013/0072917 A1 | 3/2013 | Kaschke et al. |
| 2013/0076863 A1 | 3/2013 | Rappel |
| 2013/0077048 A1 | 3/2013 | Mirlay |
| 2013/0085337 A1 | 4/2013 | Hess et al. |
| 2013/0159015 A1 | 6/2013 | O'Con |
| 2013/0197313 A1 | 8/2013 | Wan |
| 2013/0245383 A1 | 9/2013 | Friedrich et al. |
| 2013/0298208 A1 | 11/2013 | Ayed |
| 2013/0331730 A1 | 12/2013 | Fenech et al. |
| 2014/0005488 A1 | 1/2014 | Charles et al. |
| 2014/0081659 A1 | 3/2014 | Nawana et al. |

(56) References Cited

U.S. PATENT DOCUMENTS

| | | | |
|---|---|---|---|
| 2014/0168785 A1* | 6/2014 | Belgum | G02B 21/06 359/634 |
| 2014/0168799 A1 | 6/2014 | Hurbert et al. | |
| 2014/0179998 A1 | 6/2014 | Pacey et al. | |
| 2014/0187859 A1 | 7/2014 | Leeuw et al. | |
| 2014/0198190 A1 | 7/2014 | Okumu | |
| 2014/0247482 A1 | 9/2014 | Doi et al. | |
| 2014/0275801 A1 | 9/2014 | Menchaca et al. | |
| 2014/0276008 A1 | 9/2014 | Steinbach et al. | |
| 2014/0285403 A1 | 9/2014 | Kobayashi | |
| 2014/0316209 A1 | 10/2014 | Overes et al. | |
| 2014/0327742 A1 | 11/2014 | Kiening et al. | |
| 2014/0347395 A1 | 11/2014 | Tsao et al. | |
| 2014/0362228 A1 | 12/2014 | McCloskey et al. | |
| 2014/0378843 A1 | 12/2014 | Valdes et al. | |
| 2015/0025324 A1 | 1/2015 | Wan | |
| 2015/0080982 A1 | 3/2015 | Van Funderburk | |
| 2015/0087918 A1 | 3/2015 | Vasan | |
| 2015/0094533 A1 | 4/2015 | Kleiner et al. | |
| 2015/0112148 A1 | 4/2015 | Bouquet | |
| 2015/0141755 A1 | 5/2015 | Tesar | |
| 2015/0297311 A1 | 10/2015 | Tesar | |
| 2015/0300816 A1 | 10/2015 | Yang et al. | |
| 2016/0018598 A1* | 1/2016 | Hansson | F21S 11/007 385/33 |
| 2016/0089026 A1 | 3/2016 | Heerren | |
| 2016/0139039 A1 | 5/2016 | Ikehara et al. | |
| 2016/0220324 A1 | 8/2016 | Tesar | |
| 2017/0020627 A1 | 1/2017 | Tesar | |
| 2017/0143442 A1 | 5/2017 | Tesar | |
| 2017/0258550 A1 | 9/2017 | Vazales | |
| 2018/0055348 A1 | 3/2018 | Tesar et al. | |
| 2018/0055502 A1 | 3/2018 | Charles et al. | |
| 2018/0064316 A1 | 3/2018 | Charles et al. | |
| 2018/0064317 A1 | 3/2018 | Tesar | |
| 2018/0070804 A1 | 3/2018 | Tesar | |
| 2018/0256145 A1 | 9/2018 | Tesar | |
| 2018/0353059 A1 | 12/2018 | Tesar | |
| 2018/0368656 A1 | 12/2018 | Austin et al. | |
| 2019/0046021 A1 | 2/2019 | Charles et al. | |
| 2019/0053700 A1 | 2/2019 | Tesar | |
| 2019/0380566 A1 | 12/2019 | Charles | |

FOREIGN PATENT DOCUMENTS

| | | |
|---|---|---|
| CN | 102495463 | 6/2012 |
| CN | 202920720 | 5/2013 |
| DE | 103 41 125 | 4/2005 |
| DE | 10 2010 030 285 | 12/2011 |
| DE | 10 2010 044 502 | 3/2012 |
| EP | 0 293 228 | 11/1988 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 49-009378 | 3/1974 |
| JP | 03-018891 | 1/1991 |
| JP | 06-315487 | 11/1994 |
| JP | 07-194602 | 8/1995 |
| JP | 07-261094 | 10/1995 |
| JP | 08-131399 | 5/1996 |
| JP | 2001-087212 | 4/2001 |
| JP | 2001-117049 | 4/2001 |
| JP | 2001-161638 | 6/2001 |
| JP | 2001-161640 | 6/2001 |
| JP | 2002-011022 | 1/2002 |
| JP | 3402797 | 5/2003 |
| JP | 2003-322803 | 11/2003 |
| JP | 2004-024835 | 1/2004 |
| JP | 3549253 | 8/2004 |
| JP | 2004-305525 | 11/2004 |
| JP | 2007-068876 | 3/2007 |
| JP | 2009-288296 | 12/2009 |
| JP | 4503748 | 7/2010 |
| JP | 2010-206495 | 9/2010 |
| JP | 2011-118741 | 6/2011 |
| WO | WO 87/001276 | 3/1987 |
| WO | WO 91/012034 | 8/1991 |
| WO | WO 99/017661 | 4/1999 |
| WO | WO 00/078372 | 12/2000 |
| WO | WO 01/072209 | 10/2001 |
| WO | WO 2007/047782 | 4/2007 |
| WO | WO 2008/073243 | 6/2008 |
| WO | WO 2009/051013 | 4/2009 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 3/2015 |
| WO | WO 2015/100310 | 7/2015 |
| WO | WO 2016/090336 | 6/2016 |
| WO | WO 2016/154589 | 9/2016 |
| WO | WO 2017/091704 | 6/2017 |
| WO | WO 2018/208691 | 11/2018 |
| WO | WO 2018/217951 | 11/2018 |

OTHER PUBLICATIONS

Aliaga, Daniel G.; "Image Morphing and Warping"; Department of Computer Science; Purdue University; Spring 2010; in 61 pages.

"ARRI Medical Shows SeeFront 3D Display with HD 3D Surgical Microscope"; dated Jun. 9, 2013; downloaded from http://www.seefront.com/news-events/article/arri-medical-shows-seefront-3d-display-with-hd-3d-surgical-microscope/ in 2 pages.

"Arriscope: A New Era in Surgical Microscopy"; Arriscope Brochure published May 20, 2014 in 4 pages.

AustriaMicroSystems; "AS5050: Smallest Magnetic Rotary Encoder for μA Low Power Applications"; www.austriamicrosystems.com/AS5050 printed Nov. 2012 in 2 pages.

Bayonet Lock Video; 00:16 in length; Date Unknown; Received Oct. 15, 2014 [Screenshots captured at 00:00, 00:02, 00:05, 00:08, and 00:16].

BellowsTech; "Actuators"; www.bellowstech.com/metal-bellows/actuators/ printed Jul. 17, 2012 in 4 pages.

"Carl Zeiss Unveils $99 VR One Virtual Reality Headset"; www.electronista.com/articles/15/10/10/zeiss.vr.one.able.to.accept.variety.of.smartphones.using.custom.trays printed Oct. 13, 2014 in 2 pages.

Design boom; "Bright LED"; http://www.designboom.com/project/fiber-optics-light-glove/; Sep. 28, 2007.

Fei-Fei, Li; Lecture 10: Multi-View Geometry; Stanford Vision Lab; Oct. 24, 2011; in 89 pages.

"Fuse™ . Full Spectrum Endoscopy™" ; http://www.endochoice.com.Fuse printed Oct. 7, 2013 in 3 pages.

Hardesty, Larry; "3-D Cameras for Cellphones: Clever math could enable a high-quality 3-D camera so simple, cheap and power-efficient that it could be incorporated into handheld devices"; MIT News Office; http://web.mit.edu/newsoffice/2011/lidar-3d-camera-cellphones-0105.html; Jan. 5, 2012; in 4 pages.

Hartley et al.; "Multiple View Geometry in Computer Vision: Chapter 9—Epipolar Geometry and the Fundamental Matrix"; http://www.robots/ox.ac.uk/~vgg/hzbook2/HZepipolar.pdf; Mar. 2004; 2nd Edition; Ch. 9; pp. 239-261.

Heidelberg Engineering; "MultiColor: Scanning Laser Imaging"; http://www.heidelbergengineering.com/us/products/spectralis-models/imaging-modes/multicolor/; Copyright © 2013; printed Apr. 5, 2013.

Kramer, Jennifer; "The Right Filter Set Gets the Most out of a Microscope"; Biophotonics International; Jan./Feb. 1999; vol. 6; pp. 54-58.

(56) References Cited

OTHER PUBLICATIONS

Krishna, Golden; "Watch: What Good is a Screen?"; http://www.cooper.com/author/golden_krishna as printed Jul. 9, 2014 in 62 pages.

Lang et al.; "ZEISS Microscopes for Microsurgery"; Springer-Verlag; Berlin, Heidelberg; 1981.

Leica Microsystems; "Images TrueVision Integrated 3D"; http://www.leica-microsystems.com/products/surgical-microscopes/neurosurgery-spine/details/product/truevision-integrated-3d/gallery/; Nov. 26, 2014; in 3 pages.

Leica Microsystems; "Leica Microsystems' Ophthalmic Surgical Microscopes with TrueVision 3D Technology Available Globally"; http://leica-microsystems.com/products/surgical-microscopes/neurosurgery-spine/details/product/truevision-integrated-3d/news/; Sep. 18, 2014; in 5 pages.

Lutze et al.; "Microsystems Technology for Use in a Minimally Invasive Endoscope Assisted Neurosurgical Operating System —MINOP II"; 2005; http://web.archive.org/web/20151120215151/http://www.meditec.hia.rwth-aachen.de/fileadmin/content/meditec/bilder/forschung.aktuelle_projekte/robotische/Exoscope_Aesculap/pdf; Nov. 20, 2015 in 4 pages.

Male Bayonet Video; 00:04 in length; Date Unknown; Received Oct. 10, 2014 [Screenshots captured at 00:00, 00:01, 00:02, 00:03, and 00:04].

MediTec; "MINOP II—Robotical Microscope Platform"; http:web.archive.org/web/20151120213932/http://www.meditec.hia.rwth-aachen.de/en/research/former-projects/minop-II/; Nov. 20, 2015 in 3 pages.

Melexis; "MLX75031 Optical Gesture and Proximity Sensing IC"; http://melexis.com/optical-sensors/optical-sensing.mlx75031-815.aspx?sta printed Mar. 15, 2013 in 1 page.

MMR Technologies; "Micro Miniature Refrigerators"; http://www.mmr-tech.com/mmr_overview.php; Copyright © 2011; printed Feb. 11, 2013.

Moog; "Surgical Handpieces: Therapeutic Ultrasonic Devices"; http://www.moog.com/products/surgical-hpieces/ printed Sep. 25, 2013 in 1 page.

Morita; "TwinPower Turbine® High Speed Handpieces Standard, 45°, and Ultra Series Head Designs"; J. Morita Mfg. Corp., http://www.morita.com/usa/root/img/pool/pdf/product_brochures/twinpower_brochure_I-264_0512_web.pdf; May 2012; in 20 pages.

"Narrow Band Imaging"; http://web.archive.org/web/20150701233623/https://en.wikipedia.org/wiki/Narrow_band_imaging printed Jul. 1, 2015 in 1 page.

Olympus; "Olympus Introduces the World's First and Only Monopolar, Disposable Tonsil Adenoid Debrider (DTAD)"; http://www.olympusamerica.com/corporate/corp_presscenter_headline.asp?pressNo=926; Sep. 11, 2012; in 2 pages.

OmniVision; "OV2722 full HD (1080p) product brief: 1/6-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.

Orthofix; "ProView Map System Retractors"; www.us.orthofix.com/products/previewtractors.asp?cid=39; Copyright © 2010; printed Apr. 1, 2013.

OrtusTech; "Sample Shipment Start: World's Smallest Size Full-HD Color TFT LCD"; http://ortustech.co.jp/english/notice/20120427.html printed May 22, 2012 in 2 pages.

"Portion"; Definition; American Heritage® Dictionary of the English Language; Fifth Edition; 2016; Retrieved Apr. 12, 2018 from https://www.thefreedictionary.com/portion in 1 page.

Purcher, Jack; "Apple Wins a Patent for an Oculus Rift-Like Display System"; http://www.patentlyapple.com/patently-apple/2014/09/apple-wins-a-patent-for-an-oculus-rift-like-display-system.html; Sep. 9, 2014.

Rustum, Dr. Abu; ICG Mapping Endometrial Cancer; Pinpoint Endometrium Ca Lenfedenektomi MSKCC May 2013; Memorial Sloan Kettering Cancer Center; May 2013; Published to YouTube.com Sep. 1, 2013; in 2 pages; http://web.archive.org/web/20150402210857/https://www.youtube.com/watch?v=DhVhvaUCe4I.

Saab, Mark; "Applications of High-Pressure Balloons in the Medical Device Industry"; http://www.ventionmedical.com/documents/medicalballoonpaper.pdf; Copyright © 1999; in 19 pages.

Savage, Lynn; "Sound and Light, Signifying Improved Imaging"; www.photonics.com/Article.aspx?AID=45039; Nov. 1, 2010; in 6 pages.

Sun et al.; "Neurotoxin-Directed Synthesis and in Vitro Evaluation of Au Nanoclusters"; RSC Advances, 2015; vol. 5, No. 38; pp. 29647-29652.

Timm, Karl Walter; "Real-Time View Morphing of Video Streams"; University of Illinois; Chicago, Illinois; 2003; in 168 pages.

TrueVision Microscopes; http://truevisionmicroscopes.com/images/productsnew/0810a-f.jpg; printed Nov. 26, 2014 in 1 page.

TrueVision; "About TrueVision"; http://web.archive.org/web/20071208125103/http://www.truevisionsys.com/about.html; as viewed Dec. 8, 2007 in 2 pages.

TrueVision; "Leica Microsystems and TrueVision® 3D Surgical create the first 3D digital hybrid microscope"; Press Release; Oct. 5, 2012; in 2 pages.

TrueVision; "TrueVision Technology"; http://web.archive.org/web/20071208125125/http://www.truevisionsys.com/technology.html; as viewed Dec. 8, 2007 in 2 pages.

Whitney et al.; "Pop-up book MEMS"; Journal of Micromechanics and Microengineering; Oct. 14, 2011; vol. 21; No. 115021; in 7 pages.

Wikipedia; "Zoom Lens"; http://en.wikipedia.org/wiki/Optical_Zoom; printed Oct. 7, 2014 in 3 pages.

Zeiss; "Informed for Medical Professionals, Focus: Fluorescence"; Carl Zeiss; 2nd Issue; Oct. 2006; 30-801-LBW-GFH-X-2006; Printed in Germany; in 32 pages.

Zeiss; "Ophthalmic Surgery in Its Highest Form, OPMI® VISU 210"; Carl Zeiss, 2005, 30-097/III-e/USA Printed in Germany AW-TS-V/2005 Uoo; in 19 pages.

Zeiss; "SteREO Discovery. V12, Expanding the Boundaries"; Carl Zeiss, Sep. 2004; 46/0008 e Sep. 2004, in 6 pages.

Zeiss; "Stereomicroscopes: Stemi SV 6, SV 11, SV 11 Apo"; The Profile; 1999; in 30 pages.

Zeiss; "Time for a Change: OPMI® pico for ENT"; Carl Zeiss, 2005, 30-451/III-e Printed in Germany LBW-TS-V/2005 Uoo, in 8 pages.

Zhang, Michael; "LIFX: A WiFi-Enabled LED Bulb that May Revolutionize Photographic Lighting"; http://www.petapixel.com/2012/09/22/lifx-a-wifi-led-bulb-that-may-revolutionize-photographic-lighting/ printed Sep. 28, 2012 in 9 pages.

Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr; Aug. 11, 2015 in 5 pages.

Preliminary Amendment in U.S. Appl. No. 16/357,081, dated Sep. 4, 2019.

Official Communication in European Application No. 13808996.6, dated Jan. 4, 2016.

Official Communication in European Application No. 13808996.6, dated Apr. 14, 2016.

Official Communication in European Application No. 13808996.6, dated Feb. 21, 2017.

Official Communication in European Application No. 13808996.6, dated Jun. 6, 2017.

Official Communication in European Application No. 13808996.6, dated Jun. 15, 2018.

Official Communication in European Application No. 13808996.6, dated May 13, 2019.

Official Communication in Japanese Application No. 2015-520471, dated May 9, 2017.

Official Communication in Japanese Application No. 2015-520471, dated Nov. 21, 2017.

Notice of Decision or Rejection in Japanese Application No. 2015-520471, dated Jul. 24, 2018.

International Search Report and Written Opinion in PCT Application No. PCT/US2013/047972, dated Jan. 3, 2014.

(56) References Cited

OTHER PUBLICATIONS

International Preliminary Report on Patentability in PCT Application No. PCT/US2013/047972, dated Jan. 8, 2015.
Preliminary Amendment in U.S. Appl. No. 15/483,995, dated Nov. 21, 2017.
Office Action in U.S. Appl. No. 15/483,995, dated Mar. 9, 2018.
Amendment in U.S. Appl. No. 15/483,995, dated Sep. 7, 2018.
Final Office Action in U.S. Appl. No. 15/483,995, dated Nov. 29, 2018.
Amendment in U.S. Appl. No. 15/483,995, dated May 28, 2019.
Office Action in U.S. Appl. No. 15/483,995, dated Jun. 13, 2019.
Office Action in U.S. Appl. No. 15/645,589, dated Feb. 9, 2018.
Amendment in U.S. Appl. No. 15/645,589, dated Aug. 7, 2018.
Final Office Action in U.S. Appl. No. 15/645,589, dated Nov. 28, 2018.
Amendment in U.S. Appl. No. 15/645,589, dated May 28, 2019.
Office Action in U.S. Appl. No. 15/645,589, dated Jun. 13, 2019.
Preliminary Amendment filed in U.S. Appl. No. 16/036,665, dated Nov. 1, 2018.
Office Action in U.S. Appl. No. 15/626,516, dated Mar. 14, 2018.
Amendment in U.S. Appl. No. 15/626,516, dated Sep. 13, 2018.
Final Office Action in U.S. Appl. No. 15/626,516, dated Jan. 15, 2019.
Response in U.S. Appl. No. 15/626,516, dated Jul. 15, 2019.
Restriction Requirement in U.S. Appl. No. 15/495,484, dated May 14, 2019.
Amendment in U.S. Appl. No. 15/589,058, dated Nov. 15, 2017.
Office Action in U.S. Appl. No. 15/589,058, dated Dec. 8, 2017.
Amendment in U.S. Appl. No. 15/589,058, dated Jun. 7, 2018.
Final Office Action in U.S. Appl. No. 15/589,058, dated Aug. 27, 2018.
Amendment in U.S. Appl. No. 15/589,058, dated Feb. 26, 2019.
Office Action in U.S. Appl. No. 15/589,058, dated Mar. 5, 2019.
Amendment in U.S. Appl. No. 15/589,058, dated Sep. 5, 2019.
Official Communication in European Application No. 14800423.7, dated Feb. 8, 2017.
International Search Report and Written Opinion in PCT Application No. PCT/US2014/038839, dated Oct. 17, 2014.
International Preliminary Report on Patentability in PCT Application No. PCT/US2014/038839, dated Dec. 3, 2015.
Preliminary Amendment in U.S. Appl. No. 16/042,318, dated Nov. 8, 2018.
Office Action in U.S. Appl. No. 16/042,318, dated May 8, 2019.
Preliminary Amendment in U.S. Appl. No. 14/491,935, dated Feb. 5, 2015.
Restriction Requirement in U.S. Appl. No. 14/491,935, dated Sep. 8, 2017.
Restriction Requirement and Election of Species Response in U.S. Appl. No. 14/491,935, dated Jan. 8, 2018.
Office Action in U.S. Appl. No. 14/491,935, dated May 13, 2019.
Partial Supplementary European Search Report in European Application No. 14845427.5, dated May 4, 2017.
Extended European Search Report in European Application No. 14845427.5, dated Aug. 8, 2017.
Extended European Search Report in European Application No. 14846410.0, dated Jun. 23, 2017.
Official Communication in European Application No. 14846410.0, dated Jul. 18, 2018.
Official Communication in European Application No. 14846410.0, dated Mar. 20, 2019.
Official Communication in Japanese Application No. 2016-544032, dated Jun. 26, 2018.
International Search Report and Written Opinion in PCT Application No. PCT/US2014/056643, dated Dec. 11, 2014.
International Preliminary Report on Patentability and Written Opinion in PCT Application No. PCT/US2014/056643, dated Mar. 31, 2016.
Invitation to Pay Additional Fees in PCT Application No. PCT/US2014/056681, dated Jan. 14, 2015.
International Search Report and Written Opinion in PCT Application No. PCT/US2014/056681, dated Mar. 20, 2015.
International Preliminary Report on Patentability and Written Opinion in PCT Application No. PCT/US2014/056681, dated Mar. 31, 2016.
Preliminary Amendment in U.S. Appl. No. 14/581,779, dated Jul. 6, 2015.
Restriction Requirement in U.S. Appl. No. 14/581,779, dated Oct. 31, 2017.
Restriction Requirement and Election of Species Response in U.S. Appl. No. 14/581,779, dated Jan. 2, 2018.
Office Action in U.S. Appl. No. 14/581,779, dated Apr. 24, 2018.
Amendment in U.S. Appl. No. 14/581,779, dated Sep. 24, 2018.
Final Office Action in U.S. Appl. No. 14/581,779, dated Jan. 4, 2019.
Amendment in U.S. Appl. No. 14/581,779, dated Jul. 2, 2019.
Office Action in U.S. Appl. No. 14/581,779, dated Aug. 5, 2019.
Extended European Search Report in European Application No. 14873324.9, dated Aug. 25, 2017.
Official Communication in Japanese Application No. 2016-542194, dated Nov. 6, 2018.
Decision of Rejection in Japanese Application No. 2016-542194, dated May 14, 2019.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Preliminary Report on Patentability and Written Opinion in PCT Application No. PCT/US2014/072121, dated Jul. 7, 2016.
Preliminary Amendment in U.S. Appl. No. 14/960,276, dated Apr. 18, 2016.
Office Action in U.S. Appl. No. 14/960,276, dated Jul. 28, 2017.
Amendment in U.S. Appl. No. 14/960,276, dated Jan. 26, 2018.
Office Action in U.S. Appl. No. 14/960,276, dated Mar. 8, 2018.
Amendment in U.S. Appl. No. 14/960,276, dated Sep. 7, 2018.
Office Action in U.S. Appl. No. 14/960,276, dated Nov. 2, 2018.
Amendment in U.S. Appl. No. 14/960,276, dated May 2, 2019.
Final Office Action in U.S. Appl. No. 14/960,276, dated Jun. 7, 2019.
Extended European Search Report in European Application No. 15865454.1, dated Jun. 27, 2018.
International Search Report and Written Opinion in PCT Application No. PCT/US2015/064133, dated Feb. 9, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
Office Action in U.S. Appl. No. 15/081,653, dated Mar. 28, 2018.
Amendment in U.S. Appl. No. 15/081,653, dated Sep. 27, 2018.
Final Office Action in U.S. Appl. No. 15/081,653, dated Nov. 16, 2018.
Final Amendment in U.S. Appl. No. 15/081,653, dated May 15, 2019.
Office Action in U.S. Appl. No. 15/081,653, dated Jul. 12, 2019.
Extended European Search Report in European Application No. 16769809.1, dated Nov. 23, 2018.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Preliminary Amendment in U.S. Appl. No. 15/360,565, dated Feb. 6, 2017.
Office Action in U.S. Appl. No. 15/360,565, dated Aug. 10, 2018.
Amendment in U.S. Appl. No. 15/360,565, dated Feb. 8, 2019.
Office Action in U.S. Appl. No. 15/360,565, dated May 22, 2019.
Extended European Search Report in European Application No. 16869253.1, dated May 29, 2019.
Invitation to Pay Additional Fees in PCT Application No. PCT/US2016/063549, dated Feb. 2, 2017.

(56) References Cited

OTHER PUBLICATIONS

International Search Report and Written Opinion in PCT Application No. PCT/US2016/063549, dated Apr. 14, 2017.
International Preliminary Report on Patentability and Written Opinion in PCT Application No. PCT/US2016/063549, dated Jun. 7, 2018.
International Search Report and Written Opinion in PCT Application No. PCT/US2018/031442, dated Sep. 14, 2018.
International Search Report and Written Opinion in PCT Application No. PCT/US2018/034227, dated Jul. 30, 2018.
Official Communication in Japanese Application No. 2018-218745, dated Feb. 25, 2020.
Amendment in U.S. Appl. No. 15/483,995, dated Dec. 12, 2019.
Final Office Action in U.S. Appl. No. 15/483,995, dated Feb. 20, 2020.
Office Action in U.S. Appl. No. 15/645,589, dated Dec. 26, 2019.
Preliminary Amendment filed in U.S. Appl. No. 16/036,665, dated Sep. 5, 2019.
Office Action in U.S. Appl. No. 16/036,665, dated Sep. 26, 2019.
Amendment filed in U.S. Appl. No. 16/036,665, dated Mar. 26, 2020.
Amendment in U.S. Appl. No. 15/626,516, dated Jan. 24, 2020.
Notice of Allowance in U.S. Appl. No. 15/626,516, dated Mar. 9, 2020.
Response to Restriction Requirement in U.S. Appl. No. 15/495,484, dated Nov. 13, 2019.
Office Action in U.S. Appl. No. 15/495,484, dated Nov. 27, 2019.
Restriction Requirement in U.S. Appl. No. 15/948,842, dated Jan. 22, 2020.
Preliminary Amendment filed in U.S. Appl. No. 15/724,100, dated Jun. 5, 2018.
Office Action in U.S. Appl. No. 15/724,100, dated Oct. 9, 2019.
Amendment filed in U.S. Appl. No. 15/724,100, dated Apr. 9, 2020.
Amendment in U.S. Appl. No. 14/491,935, dated Nov. 13, 2019.
Final Office Action in U.S. Appl. No. 14/491,935, dated Feb. 24, 2020.
Amendment in U.S. Appl. No. 14/960,276, dated Dec. 6, 2019.
Notice of Allowance in U.S. Appl. No. 14/960,276, dated Dec. 19, 2019.
Corrected Notice of Allowability in U.S. Appl. No. 14/960,276, dated Feb. 12, 2020.
Amendment in U.S. Appl. No. 15/081,653, dated Jan. 10, 2020.
Final Office Action in U.S. Appl. No. 15/081,653, dated Jan. 31, 2020.
Amendment in U.S. Appl. No. 15/360,565, dated Nov. 21, 2019.
Office Action in U.S. Appl. No. 15/360,565, dated Jan. 30, 2020.
International Preliminary Report on Patentability and Written Opinion in PCT Application No. PCT/US2018/031442, dated Nov. 21, 2019.
International Preliminary Report on Patentability and Written Opinion in PCT/US2018/034227, dated Dec. 5, 2019.
Office Action in U.S. Appl. No. 16/357,081, dated Jul. 8, 2020.
Amendment in U.S. Appl. No. 15/483,995, dated Aug. 19, 2020.
Office Action in U.S. Appl. No. 15/483,995, dated Sep. 4, 2020.
Amendment in U.S. Appl. No. 15/645,589, dated Jun. 26, 2020.
Notice of Allowance in U.S. Appl. No. 15/645,589, dated Jul 14, 2020.
Office Action in U.S. Appl. No. 16/036,665, dated Jul. 13, 2020.
Notice of Allowance in U.S. Appl. No. 15/626,516, dated Jun. 29, 2020.
Amendment in U.S. Appl. No. 15/495,484, dated May 27, 2020.
Notice of Allowance in U.S. Appl. No. 15/495,484, dated Jun. 16, 2020.
Response to Restriction Requirement in U.S. Appl. No. 15/948,842, dated Jul. 21, 2020.
Office Action in U.S. Appl. No. 15/948,842, dated Aug. 24, 2020.
Office Action in U.S. Appl. No. 15/724,100, dated Apr. 22, 2020.
Amendment in U.S. Appl. No. 15/724,100, dated Jun. 22, 2020.
Notice of Allowance in U.S. Appl. No. 15/724,100, dated Jul. 6, 2020.
Amendment in U.S. Appl. No. 14/491,935, dated Aug. 24, 2020.
Notice of Allowance in U.S. Appl. No. 14/491,935, dated Sep. 2, 2020.
Amendment in U.S. Appl. No. 14/581,779, dated Feb. 4, 2020.
Final Office Action in U.S. Appl. No. 14/581,779, dated Apr. 29, 2020.
Amendment in U.S. Appl. No. 15/081,653, dated Jul. 30, 2020.
Office Action in U.S. Appl. No. 15/081,653, dated Sep. 17, 2020.
Amendment in U.S. Appl. No. 15/360,565, dated Jul. 29, 2020.
Notice of Allowance in U.S. Appl. No. 15/360,565, dated Aug. 13, 2020.
Burle Industries, Technical Memorandum 100—Fiber Optics: Theory and Applications, archived Feb. 21, 2007, in 20 pages https://web.archive.org/web/20070221125354/http://www.burle.com/cgi-bin/byteserver.pl/pdf/100r.pdf.

* cited by examiner

Mode A

Mode B

Mode C

Mode D

VARIABLE LIGHT SOURCE

CROSS-REFERENCE TO RELATED APPLICATIONS

This application claims the benefit of priority to U.S. Provisional Appl. No. 62/503,262 filed May 8, 2017 and to U.S. Provisional Appl. No. 62/517,089 filed Jun. 8, 2017, both of which are incorporated in their entireties by reference herein.

BACKGROUND

Field

This disclosure relates generally to light sources such as for surgical visualization. This light source may be adjustable so as to provide the desired illumination. The light source may comprise one or more solid-state light sources such as LEDs and/or laser diodes, which may potentially be coupled to fiber optics in some cases.

Description of the Related Art

Surgical visualization systems can assist healthcare providers visualize a surgical site during surgery. Such surgical visualization systems may include one or more types of cameras. Illumination can also be provided to the surgical site to enhance viewing and to assist in the visualization of surgical sites. Additionally, the spectral distribution of such illumination may be suitably tuned to enhance visualization. Such illumination may potentially be varied in different circumstances. Visualization systems may include cameras including but not limited to cameras that provide surgical microscope views, endoscopes, cameras on retractors, cameras on surgical tools, proximal cameras, exoscopes, etc. The visualization systems may include binocular displays that may include one or more displays (e.g., monitors) and may be configured to provide 2D or 3D viewing.

SUMMARY

Various examples described herein include light sources that can provide light that is directed to a surgical site. The light source can be a variable light source that can be adjusted to provide different spectral distributions. The light source can therefore be tuned to provide the desired type of lighting.

The light source may include one or more solid state emitters such as Light Emitting Diodes (LEDs) and/or lasers (e.g., laser diodes). These LEDs may be white LEDs and/or color LED's such as red green and blue LEDs. Other colors LEDs as well as other types of light sources may be employed. The light from the light sources can be combined to provide an aggregate beam that is used to illuminate the surgical site.

Light from the one or more light sources and be tuned with a tunable filter that tailors the spectral distribution. Such tunable filters may comprise a filter such as an interference filter that is tilted to alter the spectral characteristics of the filter.

Light from the various emitters may be passed through different tunable filters to control the spectral distribution of the contributions of light from the different emitters. In this manner, the aggregate beam that is directed onto the surgical site may be tailored to provide the desired spectral characteristics.

Optical fiber may be employed at some stage to deliver the light to the surgical site. For example, the light from the emitters, tuned by the tunable filters and combined may be coupled into fiber optics. Light propagated through the fiber optics maybe directed onto the surgical site.

Accordingly, certain examples described herein include efficient, high-intensity, solid-state light sources such as LEDs and/or laser diodes that provide light that is spectrally tuned and collected and directed possibly into optical fiber or other optics that collects the light. Example designs may thus provide variable light rendering using small high-intensity light sources that propagate light through a collection of pathways for illuminating the receiving end of a fiber optics illumination conduit or light conduit. More particularly, certain embodiments may provide variable light rendering using small high-intensity light sources that output light that is directed to one or more variable filters via a collection of pathways for illuminating one end of a fiber optics illumination conduit or light conduit. Certain examples combine phosphor-coated LED high-intensity light sources and colored light sources (e.g., laser diodes) for excitation via a collection of pathways for illuminating one end of a fiber optics illumination conduit or light conduit.

Various designs may be configured to provide the user with choices for the illumination modes. The light source, for example, may be adjusted by the user to provide different types of illumination having different spectral make-up. The optical spectrum of the light provided may, for example, be adjusted by controlling which light sources is used to provide light as well as possibly by tuning light from the one or more light sources using the tunable filters.

Various designs may include a communication system to receive instructions from the user to control the illumination mode and/or to control the spectral distribution of the light output by the light source. A communication system may also provide communication to one or more displays and/or one or more cameras.

Various designs include an illumination device comprising at least one sub-source comprising a plurality of light emitters configured to produce light flux. The illumination device further comprises a plurality of optical fibers, each optical fiber of the plurality of optical fibers comprising a first end portion configured to receive the light flux from a corresponding light emitter and a second end portion configured to emit the received light flux. The light emitters are arranged in a first pattern, the first end portions are arranged in the first pattern, and the second end portions are arranged in a second pattern different from the first pattern.

BRIEF DESCRIPTION OF THE DRAWINGS

FIG. 3 illustrates an example Mode A of the light source of FIG. 2A configured to output an approximation of D65 light.

FIG. 4 illustrates an example Mode B of the light source of FIG. 2A configured to output narrow band illumination.

FIG. 5 illustrates an example Mode C of the light source of FIG. 2A configured to output an approximation of D65 light and near IR excitation.

FIG. 6 illustrates an example Mode D of the light source of FIG. 2A configured to output D light excitation.

DETAILED DESCRIPTION

Figure 1A:
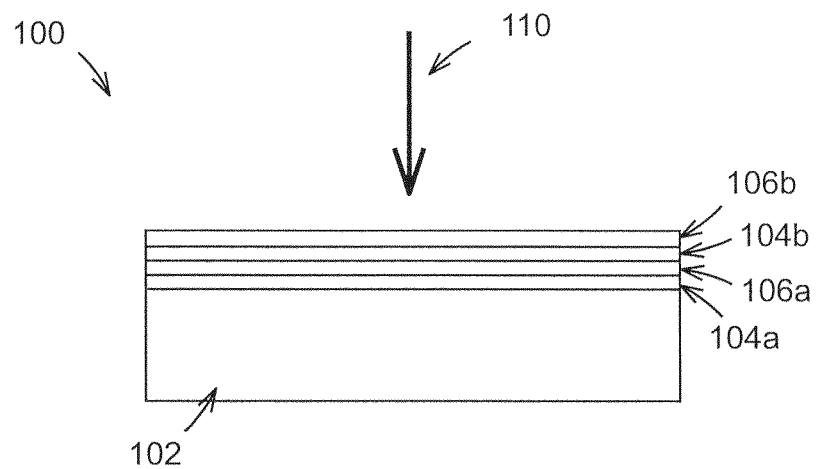
FIG. 1A is a schematic diagram of an example spectral filter such as a bandpass interference filter comprising a plurality of layers disposed on a substrate.

Various examples described herein include light sources that can provide light that is directed to a surgical site. These light sources may be used to illuminate a surgical site while one or more cameras capture images such as video images of the surgical site and may be used for diagnosis, general medical lighting, or other procedures or activities. Cameras and systems for imaging the surgical site may include, for example, surgical microscope view cameras, endoscopes, cameras on retractors, cameras on surgical tools, proximal cameras, exoscopes, etc. Such surgical visualization systems may display images such as video using a binocular display assembly that include displays that provide views of images obtained from the camera or cameras. The surgical visualization systems may switch from viewing an image or video input from one camera to another or show multiple views simultaneously. Moreover, the light source may be automatically varied when switching from displaying a view from one camera to a view from another camera.

Illumination may facilitate enhanced visualization of the surgical site such as obtained by video camera. Light, for example, can be provided to the surgical site via optical fiber. In some cases where an endoscope is employed to capture images within the body, the light may be provided to the surgical site via the endoscope. In certain embodiments, the light can be provided via fiber optics in various ways. For example, fiber optics can be integrated into an endoscope configured to be inserted into a body via a natural opening or lumen in the body, or through a surgically induced opening in the body. For another example, fiber optics can be integrated into an exoscope (e.g., an imaging device that "stands off" from the patient and provides a surgery site view) or a camera providing surgical microscope views. For another example, fiber optics can be brought near the patient to supplement overhead surgical lighting (e.g., used by the physician sans optical devices or with non-illuminated magnification devices, such as loupes, or to supplement other medical imaging modalities such as endoscopes, exoscopes, or cameras providing surgical microscope views).

The light source can be a variable light source that can be adjusted to provide different spectral distributions. The light source can therefore be tuned to provide the desired type of lighting. In particular, it can be advantageous to provide a light source having a transition (e.g. gradual transition) or a variable change of the output spectral power distribution such as a gradual transition or a variable change between a white light rendering and narrow band imaging.

Certain examples described herein provide such light sources utilizing filters that have a spectral characteristic that varies with orientation such as tilt. Interference filters, for example, have a spectral response, such as spectral transmission or refection that varies with angle of orientation. Accordingly, by varying the orientation of these filters, the spectral distribution of the light interacting with the filter can be adjusted or tuned.

In certain embodiments, the light source can operate in three modes, as well as in combinations of these three modes. The three modes for certain embodiments can be described as follows:

Mode 1: White light for general medical or surgical illumination (e.g., "surface" based illumination). This mode can include the ability to illuminate a scene in a D65-near-equivalent matter, and can include the ability to modify the color temperature of the "white light" (e.g., adjusting the wavelength range of the white light to make it warmer or cooler).

Mode 2: Specialized "surface" based illumination (e.g., short wavelengths; blue waveband; green waveband; D-light; light compatible with photodynamic diagnosis (PDD); light which helps visualize changes in the epithelium, in either of two or more sub-modes). For example, this mode can include a sub-mode comprising activating both blue and green channels in a manner suitable for narrow band imaging (NBI), and can include a sub-mode comprising activating only blue light for a D-light mode.

Mode 3: "Deep penetrating" illumination comprising near infrared (NIR) illumination or excitation. This mode can include either or both of two sub-modes: a sub-mode with a broader-based NIR illumination to reveal below the surface structures in tissue, and a sub-mode with a narrow NIR illumination to excite a dye or other material, which can be used in conjunction with blocking filters.

Figure 1B:
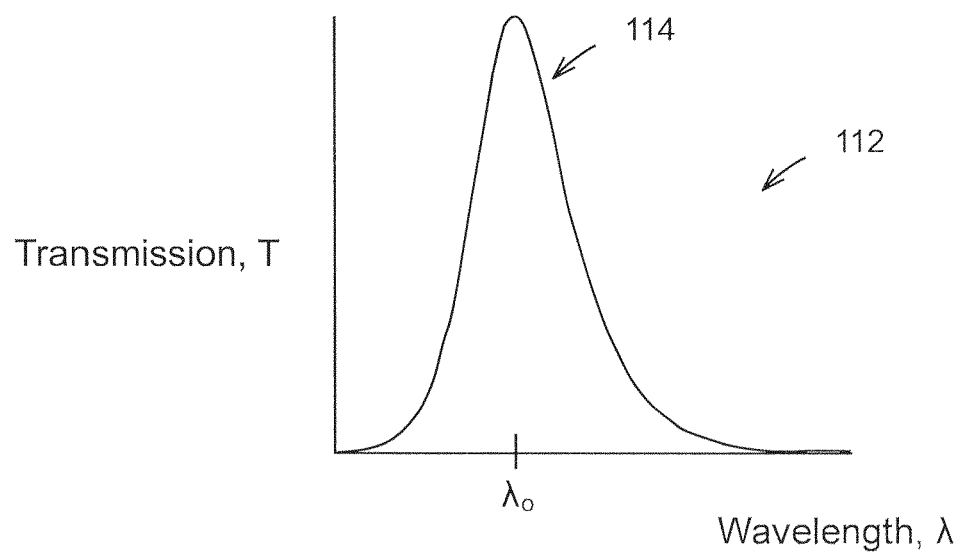
FIG. 1B is a schematic illustration of a plot of the optical transmission versus wavelength (both in arbitrary units) for the filter of FIG. 1A showing a peak in optical transmission.

FIG. 1A schematically illustrates a filter 100 such as an interference filter that can be tilted to alter the spectral characteristics of the filter. The filter 100 comprises a substrate 102 on which a plurality of layers 104a, 104b, 106a 106b are disposed. In some designs, a portion of the layers 104a, 104b may comprise a first material and a portion of the layers 106a 106b may comprise a second material. As illustrated, the layers 104a, 104b, 106a 106b may alternate between the first material and the second material. The layers 104a, 104b, 106a 106b may have specific thickness so as to cause optical interference of incident light 110 that is reflected from each of the layers that results in either constructive or destructive interference and the desired output. In some designs, filter 100 is designed for a specific wavelength and the layers 104a, 104b, 106a 106b may have specific thickness, for example, such as a quarter of the wavelength. The layers 104a, 104b, 106a 106b, however, are configured to provide optical interference that results in high or low transmission (or reflectivity) for different wavelengths. In this manner, a desired spectral responsivity maybe designed for the filter 100. For example, the materials, thickness, and arrangement of the layers 104a, 104b, 106a 106b may be configured to provide a specific spectral characteristic such as a pass band. Accordingly, in some examples, the filter 100 comprises a band pass filter configured to selectively transmit or reflect a particular wavelength when light 110 is normally incident on the filter. FIG. 1B, for example, shows a schematic drawing of a spectral distribution 112 for a band pass filter. The band pass filter has a band pass region 114 where one or more wavelengths of light 110 incident on the filter 100 at normal incidence is transmitted therethrough. This band pass region 114 is show to be centered about the center wavelength of $\lambda_0$. In contrast, the spectral responsivity 112 of the band pass filter has spectral regions above and below the band pass region 114 that provides reduced transmission in comparison to the transmission of the band pass region for wavelengths above and below than the wavelengths of the band pass region.

Figure 1C:
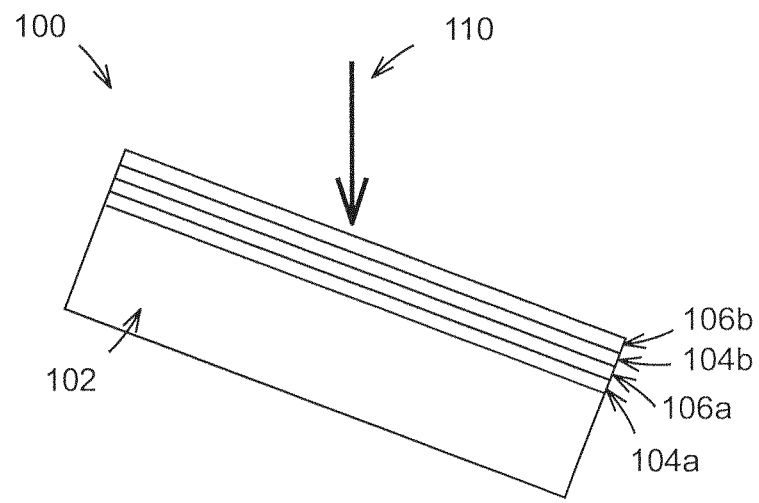
FIG. 1C is a schematic diagram of the spectral filter of FIG. 1A tilted clockwise.
Figure 1D:
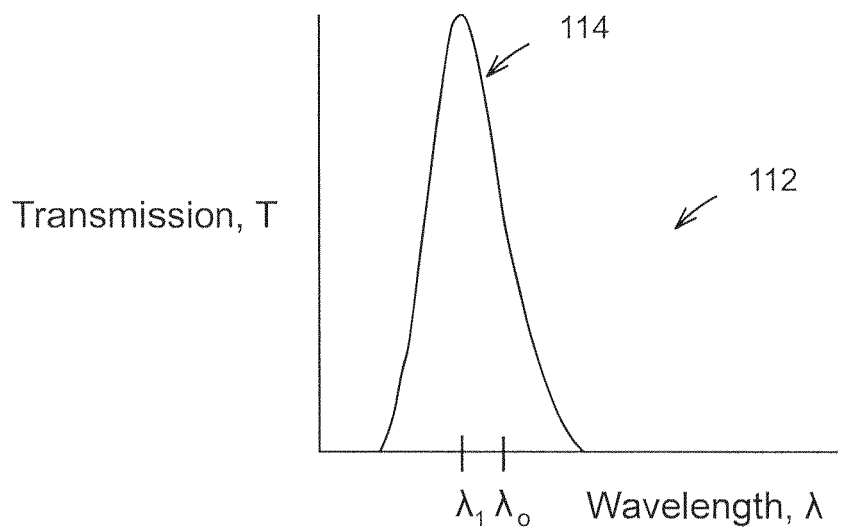
FIG. 1D is a schematic illustration of a plot of the optical transmission versus wavelength (both in arbitrary units) for the filter of FIG. 1A that is tilted thereby resulting in a shift in the peak in optical transmission.

Changing the orientation of the incident light 110 with respect to the filter 100 and the interference coating or alternatively changing the orientation of the filter with respect to the incident light can alter the spectral responsivity 112 of the filter. As illustrated in FIGS. 1C and 1D, for example, tilting the filter 100 with respect to the incident light 110 can shift the band pass region 114. In particular, this band pass region 100 shifts with tilt. The band pass region 114 for the tilted filter 100 shown in FIG. 1C, is centered about the center wavelength of $\lambda_1$, which is shifted with respect to the center wavelength of $\lambda_0$ of the un-tilted filter.

Figure 1E:
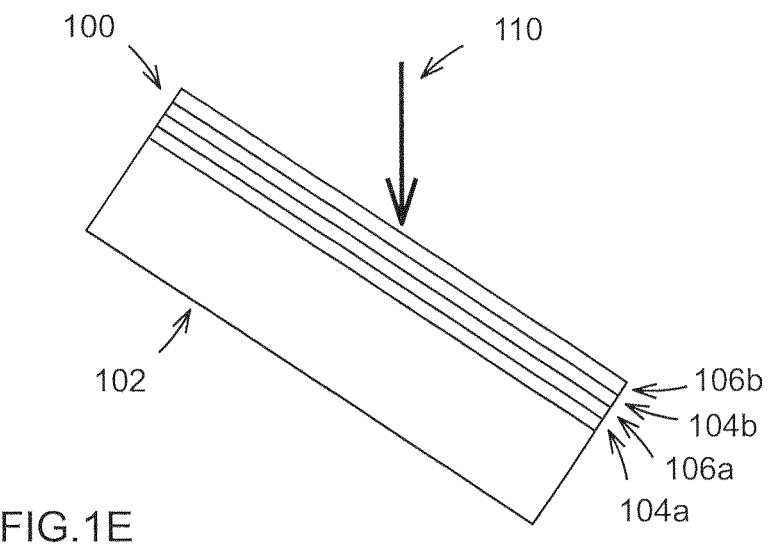
FIG. 1E is a schematic diagram of the spectral filter of FIGS. 1A and 1C further tilted.
Figure 1F:
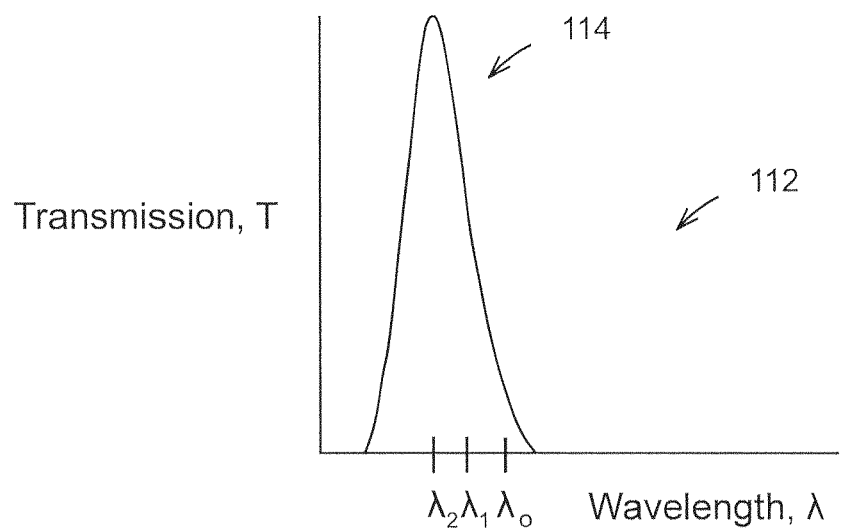
FIG. 1F is a schematic illustration of a plot of the optical transmission versus wavelength (both in arbitrary units) for the filter of FIGS. 1A and 1C that is further tilted thereby resulting in a further shift in the peak in optical transmission.

With further tilt, the spectral responsivity 112 continues to change. Further tilt of the filter 100 of FIGS. 1A and 1C is illustrated in FIGS. 1E and 1F. As shown in FIGS. 1E and 1F, for example, progressively tilting the filter 100 with respect to the incident light 110 can alter the band pass region 114 progressively more. In particular, this band pass region 114 is progressively shifted with tilt. The band pass region 114 for the tilted filter 100 shown in FIG. 1E, is centered about the center wavelength of $\lambda_2$, which is further shifted with respect to the center wavelength of $\lambda_0$ of the tilted filter of FIG. 1A and is thus shown as shifted with respect to the center wavelength of $\lambda_1$ of the tilted filter of FIG. 1C.

Accordingly, progressively tilting or reorienting the filter 100 with respect to the incident light can change the transmission or reflection properties of the filter and thus changes the spectral distribution of light transmitted or reflected from the filter. For example, if white light is transmitted through the filter 100, a first wavelength band may be selectively pass through the filter and output therefrom. If that filter 100 is tilted slightly, a second wavelength band shifted slightly in wavelength with respect to the first wavelength band may be selectively passed through the filter and output therefrom. If that filter 100 is tilted slightly more, a third wavelength band shifted slightly more in wavelength with respect to the first wavelength band may be selectively passed through the filter and output therefrom.

The interference filter 100 need not be limited to the filter shown in FIGS. 1A-1F. For example, the interference filter 100 need not be a band pass filter but may for example be a long pass filter or a short pass filter. Additionally, although four layers 104a, 104b, 106a, 106b are shown, the interference coating may include a larger or smaller number of layers. Additionally, although two types of layers 104a, 104b, 106a, 106b each comprising a different material are shown, alternately, more than two different types of layers maybe be used. For example, the optical coating can comprise three different types of layers (e.g., a first group comprising a first layer comprising a first material disposed on a substrate, a second layer comprising a second material disposed on the first layer, and a third layer comprising a third material disposed on the second layer. This sequence of layers can be repeated again in a second group comprising another first layer comprising the first material, a second layer comprising the second material, and a third layer comprising the third material as stacked over the first group of layers. The different materials can have different indices of refraction. One may have a relatively high refractive index, one a medium refractive index, and one a relatively low refractive index. Although two groups of layers are described above, the coating may include more groups. Additionally, the groups may include more or less than three layers. Other variations are also possible.

Figure 1G:
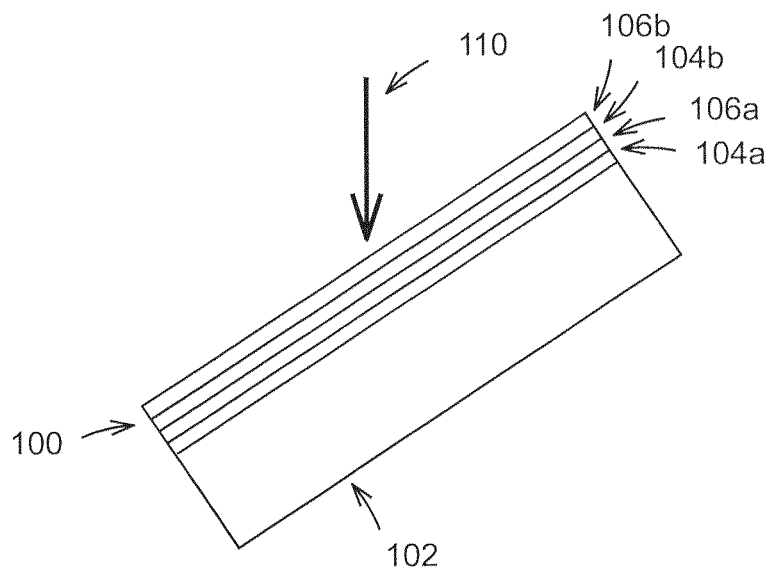
FIG. 1G is a schematic diagram of the spectral filter of FIGS. 1A, 1C, and 1E tilted in the opposite direction (counter clockwise) than the tilt (clockwise) shown in FIGS. 1C and 1E.

FIG. 1G shows the filter 100 as tilted the opposite direction (counter clockwise) than the tilt (clockwise) shown in FIGS. 1D and 1F.

The substrate 102 on which the layers are may comprise glass, plastic, or other materials. In some embodiments the filter 100 is transmissive. Accordingly, the substrate 102 may be transmissive. In other cases, the filter 100 is reflective. Likewise, although transmission spectra 112 are shown in FIGS. 1B, 1D, and 1F, these spectra may be reflective spectra and the output of the filter 100 may be reflected light that has a spectral distribution that can be modified in a gradual and continuous manner by tilting the filter.

Accordingly, actuators such as motors, piezos, etc. may be used to tilt and thereby reorient the filters in a controlled manner with respect to the incident light. Electrical signals may be applied to the actuators, e.g., motors, piezos, etc., to cause rotation. The electrical signal may be provided by electronics such as control electronics that controls the amount of tilt of the filter(s) and hence the amount of change of spectral responsivity of the filter and thus the spectral distribution of the light output (e.g., transmitted through or reflected from) the filter or filters. In certain embodiments, multiple filters (e.g., a high pass filter and a low pass filter) can be placed in a single light path. For example, the multiple filters can be stacked on a single surface, on opposite sides of a plate or element, and/or coated on a surface or element and embedded within an epoxy bond. The electronics may also control the light emitters (e.g., LEDs, laser diodes), for example, the amount of light output by the light emitter. Such electronics, may for example, control the amount of electrical power that drives the emitters.

Accordingly, illumination systems may include light sources such as LEDs that output light that is directed along one or more paths. Tunable filters such as described above may be included in the one or more paths to alter the spectrum of the light from the light sources that propagate along the one or more paths. These paths maybe brought together to provide an aggregate beam having the desired spectral distribution.

In some examples, therefore, thin film coatings, such as interference coatings, applied to one or more plane parallel plates or other substrate are placed in the paths of corresponding beams (e.g., collimated beams) and can be adjustably tilted to vary the color or waveband distribution.

Figure 1H:
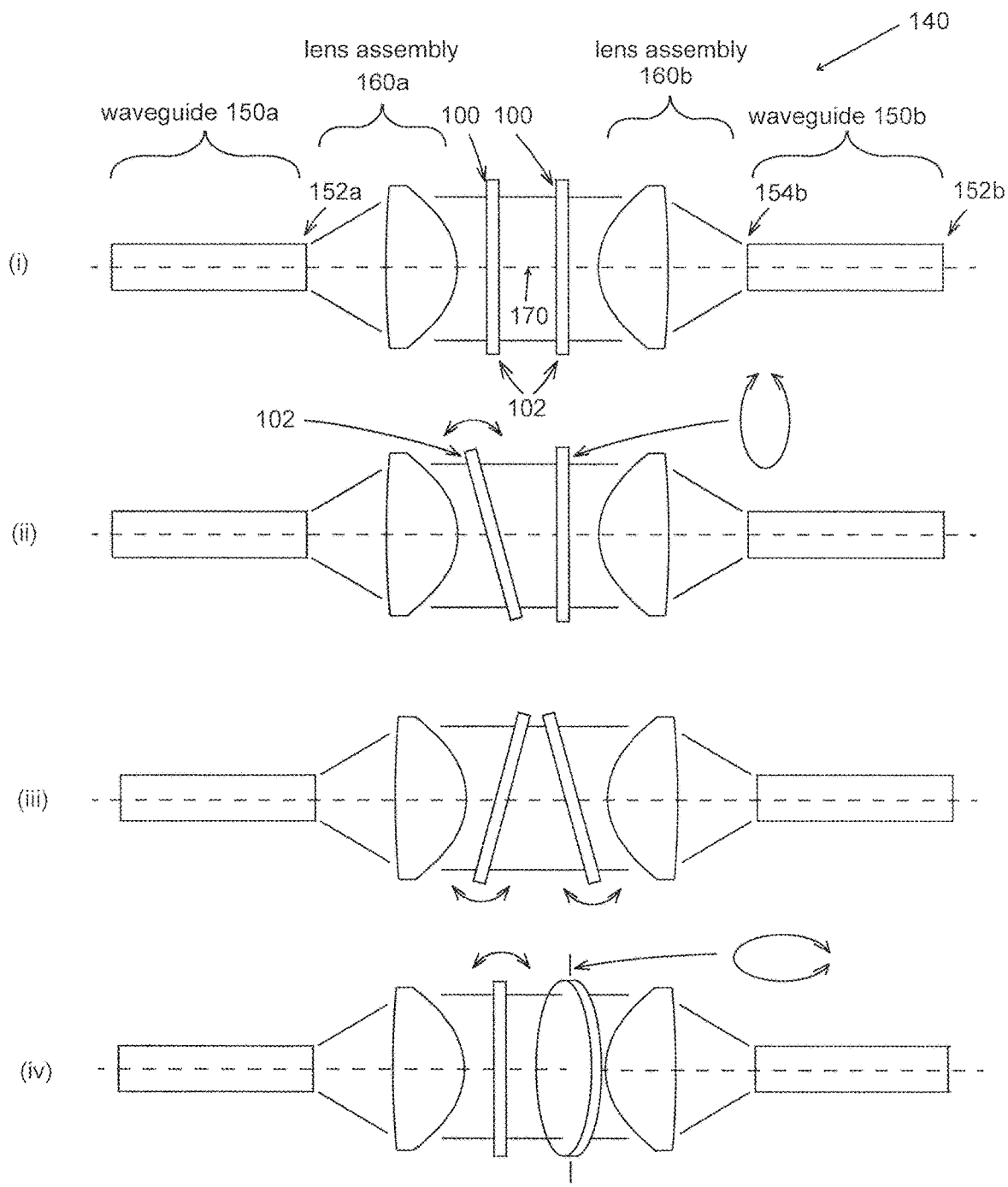
FIG. 1H schematically illustrates an example color mixing assembly comprising a plurality of filters in accordance with certain embodiments described herein.

FIG. 1H schematically illustrates an example color mixing assembly 140 comprising a plurality of filters 100 in accordance with certain embodiments described herein. The example color mixing assembly 140 may be used in the example illumination device schematically illustrated in FIG. 2A and described more fully below. The color mixing assembly 140 comprises a first waveguide 150a (e.g., glass or plastic; mixing rod; light guide or waveguide) having a first output face 152a, a first lens assembly 160a, the plurality of filters 100, a second lens assembly 160b, and a second waveguide 150b (e.g., glass or plastic; mixing rod; light guide or waveguide) having a second output face 152b and an input face 154b. The first output face 152a is in optical communication with the first lens assembly 160a. The first lens assembly 160a is in optical communication with the plurality of filters 100, the plurality of filters 100 is in optical communication with the second lens assembly 160b, and the second lens assembly 160b is in optical communication with the input face 154b of the second waveguide 150b. The plurality of filters 100 is configured to direct the light emitted by the plurality of filters 100 to the second lens assembly 160b. The second lens assembly 160b is configured to focus the light and to couple the light to the second waveguide 150b via the input face 154b of the second waveguide 150b. The second output face 152b of the second waveguide 150b is configured to direct the light to the fiber optic cables (not shown). For example, the second output face 152b can be in close proximity to the fiber optic cables. Light from the optical emitters is directed to the first waveguide 150a, propagates through the first output face 152a, through the first lens assembly 160, the plurality of filters 100, the second lens assembly 160b, and the input face 154b of the second waveguide 150b, with the resultant light emitted from the second output face 152b of the second waveguide 150b.

The first output face 152a of the first waveguide 150a is configured to emit light directed towards the first lens assembly 160a which is configured to substantially collimate the light emitted from the first output face 152a and to direct the collimated light along the optical path 170 through the plurality of filters 100. Each filter 100 of the plurality of filters 100 comprises at least one interference plate 102 having at least one dichroic coating applied to at least one face of the plate 102, and the plate 102 is configured to be controllably rotated (e.g., tilted) in at least one direction. The angular and/or rotational differences of the plates 102 are configured to be controllably adjusted such that the filters 100 controllably interact with the light received from the first lens assembly 160a to modify (e.g., shift; compress) the spectral distribution of the light in an advantageous manner. For example, referring to FIGS. 1C and 1D, the spectral distribution of the light can be shifted and compressed from λ0 to λ1.

The plurality of filters 100 has a center axis 170 along which the light is propagating from the first lens assembly 160a to the second lens assembly 160b in a region between the first lens assembly 160a and the second lens assembly 160b and the plates 102 of the plurality of filters 100 are located along the center axis 170. The various views of the color mixing assembly 140 in FIG. 1H show various example degrees of freedom in which the plates 102 may be configured to be controllably rotated (e.g., tilted). In view (i) of FIG. 1H, the two plates 102 are both generally perpendicular to the center axis 170. In view (ii) of FIG. 1H, one plate 102 is configured to be rotated about an axis perpendicular to the center axis 170 and parallel to the plate 102, and the other plate 102 is configured to be rotated about an axis parallel to the center axis 170. In view (iii) of FIG. 1H, one plate 102 is configured to be rotated about an axis perpendicular to the center axis 170 and parallel to the plate 102, and the other plate 102 is configured to be rotated about an axis perpendicular to the center axis 170 and parallel to the plate 102, with the two rotational axes parallel to one another. In view (iv) of FIG. 1H, one plate 102 is configured to be rotated about an axis perpendicular to the center axis 170 and parallel to the plate 102, and the other plate 102 is configured to be rotated about an axis perpendicular to the center axis 170 and parallel to the plate 102, with the two rotational axes perpendicular to one another.

In various embodiments, the plurality of filters 100 can comprise one or more dichroic filters. In some embodiments, the plurality of filters 100 can comprise one or more polarization components. Rotating or tilting one or more components of the plurality of filters 100 (e.g., the plate 102) about the different rotational axes can induce a spectral change in the filter output. For example, rotating or tilting one or more components of the plurality of filters 100 (e.g., the plate 102) can attenuate, reduce or extinguish a portion of the signal output from the plurality of filters 100. As another example, rotating or tilting one or more components of the plurality of filters 100 (e.g., the plate 102) can shift the spectrum of the signal output from the plurality of filters 100.

In various embodiments, the plurality of filters 100 comprising one or more dichroic filters can be sensitive to polarization of light output from the one or more light sources. In such embodiments, rotating or tilting (e.g., rotating azimuthally) the one or more components of the plurality of filters 100 (e.g., the plate 102) can change the spectral composition of the light output from the plurality of filters 100. For example, if in a particular orientation of the various components of the plurality of filters 100, the output from the plurality of filters 100 can comprise a first amount of light in a first wavelength and a second amount of light in a second wavelength. When one or more components of the plurality of filters 100 is rotated or tilted, the output from the plurality of filters 100 can include different amounts of light in the first and the second wavelengths. This effect may result because the filters may be polarization dependent in some cases. The resultant change in transmission of different wavelengths through the filter(s) can thus modify the spectral composition of the output of the filters. By increasing and/or decreasing the intensity of different wavelengths output by one or more such filters, for example, the overall shape of the spectral distribution can be altered. For example, the magnitude of certain spectral wavelengths can be reduced compared to other wavelengths. Accordingly, various optical emitters can be tailored to emit light having a desired spectral characteristic and/or intensity characteristic which when combined with rotation or tilt of the one or more components of the plurality of filters 100 can provide light with desired illumination characteristics (e.g., spectral characteristic and/or intensity characteristic).

Figure 1I:
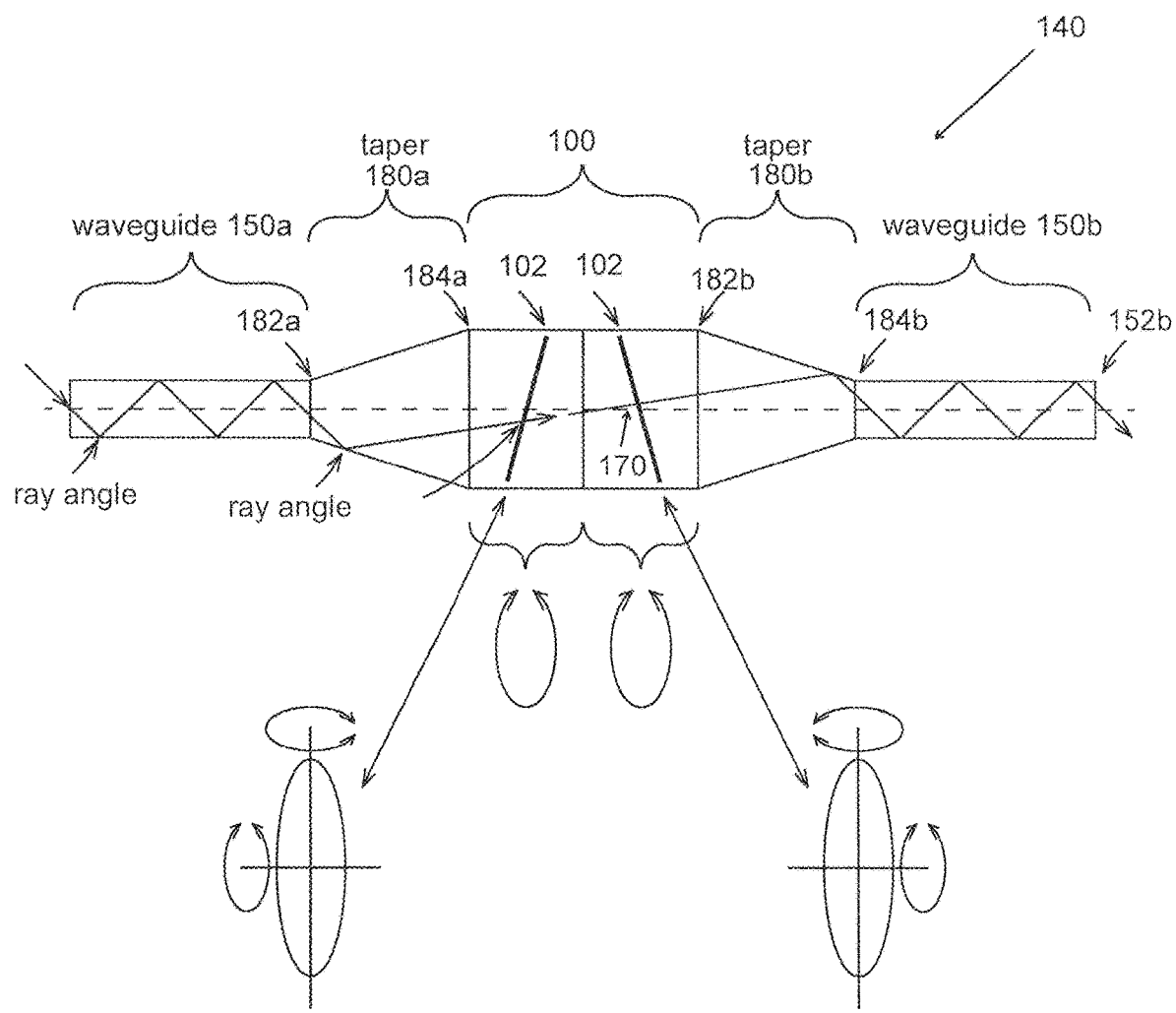
FIG. 1I schematically illustrates another example color mixing assembly comprising a plurality of filters in accordance with certain embodiments described herein.

FIG. 1I schematically illustrates another example color mixing assembly 140 comprising a plurality of filters 100 in accordance with certain embodiments described herein. The color mixing assembly 140 shown in FIG. 1I does not include airspaces or lenses through which light is transmitted while propagating through the color mixing assembly 140. As compared to the example color mixing assembly 140 of FIG. 1H, the example color mixing assembly 140 of FIG. 1I replaces the lens assemblies 160a, 160b with first and second tapers 180*a*, 180*b*. The first taper 180*a* comprises an input end 182*a* in optical communication with the output face 152*a* of the first waveguide 150*a* and an output end 184*a* in optical communication with the plurality of filters 100. The size of the input end 182*a* (e.g., diameter; width; area) is smaller than the size of the output end 184*a* (e.g., diameter; width; area) such that a numerical aperture of the input end 182*a* is smaller than a numerical aperture of the output end 184*a*. The second taper 180*b* comprises an input end 182*b* in optical communication with the plurality of filters 100 and an output end 184*b* in optical communication with the input face 154*b* of the second waveguide 150*b*. The size of the input end 182*b* (e.g., diameter; width; area) is larger than the size of the output end 184*b* (e.g., diameter; width; area) such that a numerical aperture of the input end 182*b* is larger than a numerical aperture of the output end 184*b*. Thus, the tapers 180*a*, 180*b* of FIG. 1I serve a similar function as do the lens assemblies 160*a*, 160*b* of FIG. 1H.

In certain embodiments, the reduced numerical aperture, or angular output, of the color mixing assembly 140 (e.g., whether by lens assemblies 160*a*, 160*b* of FIG. 1H or by tapers 180*a*, 180*b* of FIG. 1I) can be used to produce a more collimated flux profile permitting the plurality of filters 100 to be more efficient in modifying (e.g., shifting; compressing; blocking; passing) portions of the flux energy from the optical emitters. FIG. 1I schematically shows a light ray entering the waveguide 150*a* at an angle and traversing the length of the waveguide 150*a* until transitioning into the taper 180*a*, where upon the light ray reflects off a side wall of the taper 180*a* at a new angle associated with the taper 180*a*. The sum of the energy of the light ray remains substantially unchanged (e.g., except for small side wall losses and coupling losses).

The flux energy exiting the plurality of filters 100 is coupled to the waveguide 150*b* by the taper 180*b*. As shown in FIG. 1I, the ray paths of the light propagating through the plurality of filters 100 can be steeply angled relative to the center axis 170 of the plurality of filters 100.

Each of the two plates 102 of the plurality of filters 100 can be configured to be controllably rotated (e.g., tilted) with respect to one another, thereby permitting modification (e.g., shifting; compressing; blocking; passing) portions of the flux energy propagating through the color mixing assembly 140. For example, each of the two plates 102 can be configured to be controllably rotated (e.g., tilted) about one or more axes (e.g., the center axis 170 of the plurality of filters 100; an axis perpendicular to the center axis 170 and parallel to the plate 102; an axis perpendicular to the center axis 170).

Figure 1J:
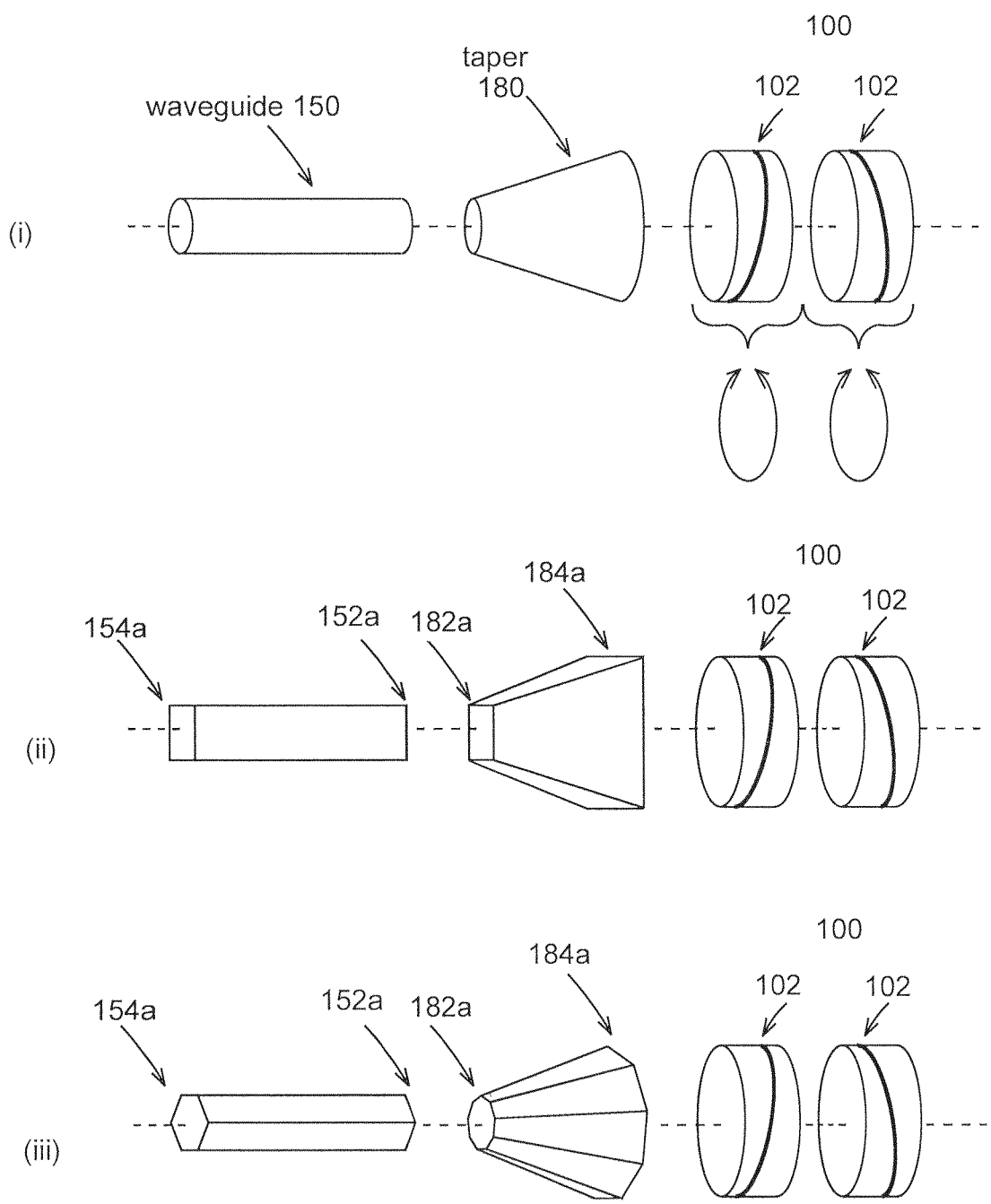
FIG. 1J schematically illustrates example portions of example color mixing assemblies in accordance with certain embodiments described herein.

FIG. 1J schematically illustrates example portions of example color mixing assemblies 140 in accordance with certain embodiments described herein. While the waveguides 150, lens assemblies 160, tapers 180, and plates 102 of certain embodiments can be cylindrical and circularly symmetric, as in view (i) of FIG. 1J, in certain other embodiments, one or more of the waveguides 150, lens assemblies 160, tapers 180, and plates 102 can include one or more flat sides. Certain such embodiments can advantageously skew the light rays, mix the flux energy, and/or integrate the flux energy propagating through the color mixing assembly 140 to generate a more even light output. For example, the four-sided waveguide 150 shown in view (ii) of FIG. 1J can provide a more even light output than can the circularly symmetric waveguide 150 shown in view (i) of FIG. 1J, and the six-sided waveguide 150 (e.g., hex rods) shown in view (iii) of FIG. 1J can provide a more even light output than can the four-sided waveguide 150. In certain embodiments, the interfaces between the larger ends of the tapers 180 with faceted sides can suffer more losses than do interfaces with the circularly symmetric tapers 180, particularly in embodiments in which the plates 102 have circular diameters. In certain embodiments, an advantageous compromise can be achieved using a six-sided waveguide 150 and a six-sided taper 180. In certain embodiments, a taper 180 having facets on one end and circularly symmetric on the other end can be used. In certain embodiments, the tapers 180 and waveguides 150 (e.g., hex rods) of FIGS. 1I and 1J can rotate axially with respect on one another and with respect to the sections containing the plates 102. To facilitate optical coupling between the rotating surfaces, a matching index fluid may be disposed between the tapers 180 and the sections containing the plates 102. In some configurations, for example, the light can propagate between the taper and the index matching fluid and between the index matching fluid and waveguide thereby reducing Fresnel reflection from the surface of the taper and the surface of the waveguide as a result of the presence of index matching fluid. The index matching fluid, may for example have an index of refraction greater than 1.0. The index matching fluid may have an index close to the index of the tapers and the waveguides.

The one or more plates (filters) can be coupled to an electrical controller configured to simultaneously change the power provided to some or all of the LEDs in groups or together as the plates are tilted. The light source can also communicate with a control device which may display spectral power distribution to a visualization display. Certain such embodiments advantageously provide high power densities using arrays or assortments of low-cost, high-output LED dies. In certain embodiments, one or more LEDs can be placed in direct contact with one or more waveguides and can direct their flux energy in the direction of the long axis of the waveguide, with the flux energy captured in the waveguide by total internal reflection.

In certain designs, for example, the illumination system or light source may contain a communication bus, which communicates with one or more cameras. The color responses can vary greatly between cameras, and in certain cases, an input profile can be provided specifically for the camera. Certain configurations can provide an illumination system that tailors its output for different cameras used in switching the resultant visualization. The illumination system may, for example, adjust the spectral or color waveband distribution depending on which camera is being used to generate the image being viewed by the user.

In certain illumination systems, the variable spectral output generated using the tilted plates can be advantageously used with corresponding filters in the one or more cameras. For example, autofluorescence and exogenous agents utilize intense excitation sources that can obscure the emission of dyes and agents used in many studies. In such circumstances, the camera can include blocking filters to be used in conjunction with the light source, and the variable output can be adjusted accordingly. For example, the cameras can include filters or detectors that are configured to block light below 700 nm, such that autofluorescence largely disappears in images with wavelengths above 700 nm, so fluorescence imaging in the infrared reduces background "noise" caused by tissue autofluorescence.

Furthermore, color rendering in normal visualization and false-color and pseudo-color rendering can benefit from variable filtering with tilted plates in some instances. For example, the color rendering in normal visualization may be more medically useful to the physician if the color temperature of the light is modified, and/or if the illumination or brightness level can be varied or modified (e.g., by excluding, enhancing, or otherwise modifying one or more portions of the waveband) by the introduction of one or more variable filters used alone or in combination with one another (e.g., blocking or passing filters). In certain embodiments, the illumination system is configured to be used with a visualization system that incorporates false color and/or pseudo-color images.

As used herein, "false color" refers to a group of color rendering methods used to display images in color which were recorded in the visible or non-visible parts of the electromagnetic spectrum, and a false-color image is an image that depicts an object in colors that differ from those a true-color image would show. A false-color image can be created using solely the visual spectrum (e.g., to accentuate color differences), and/or using data from electromagnetic radiation outside the visual spectrum (e.g., infrared, ultraviolet, X-ray), with the choice of spectral bands governed by the physical properties of the object under investigation. In addition, variants of false color (e.g., pseudo-color, density slicing, and choropleths) can be used for information visualization of either data gathered by a single grayscale channel or data not depicting parts of the electromagnetic spectrum (e.g., elevation in relief maps or tissue types in magnetic resonance imaging). In contrast to a true-color image, a false-color image sacrifices natural color rendition in order to ease the detection of features that are not readily discernible otherwise (e.g., the use of near infrared for detecting emission from an exogeneous dye; imaging tissue features hidden below the surface which are visible in the near infrared, but not visible in visible light, such as in a range of 400 nm-700 nm).

In certain designs, the illumination device can include one or more tilting planes and a mix of phosphor-converted LEDs (e.g., white LEDs; blue or purple LEDs coated with a phosphor to reemit over a broader and longer wave band range), multi-colored LEDs (e.g., a plurality of LEDs of two or more different colors), and/or one or more other excitation sources (e.g., near-IR). For example, in photodynamic therapy applications, which utilize illumination in the UV and blue regions (e.g., soret band range), suitable excitation sources can be added to the device and controlled as other modes. Additionally, in other examples, near-IR excitation sources can be used with visual illumination or narrow-band imaging (NBI).

Figure 2A:
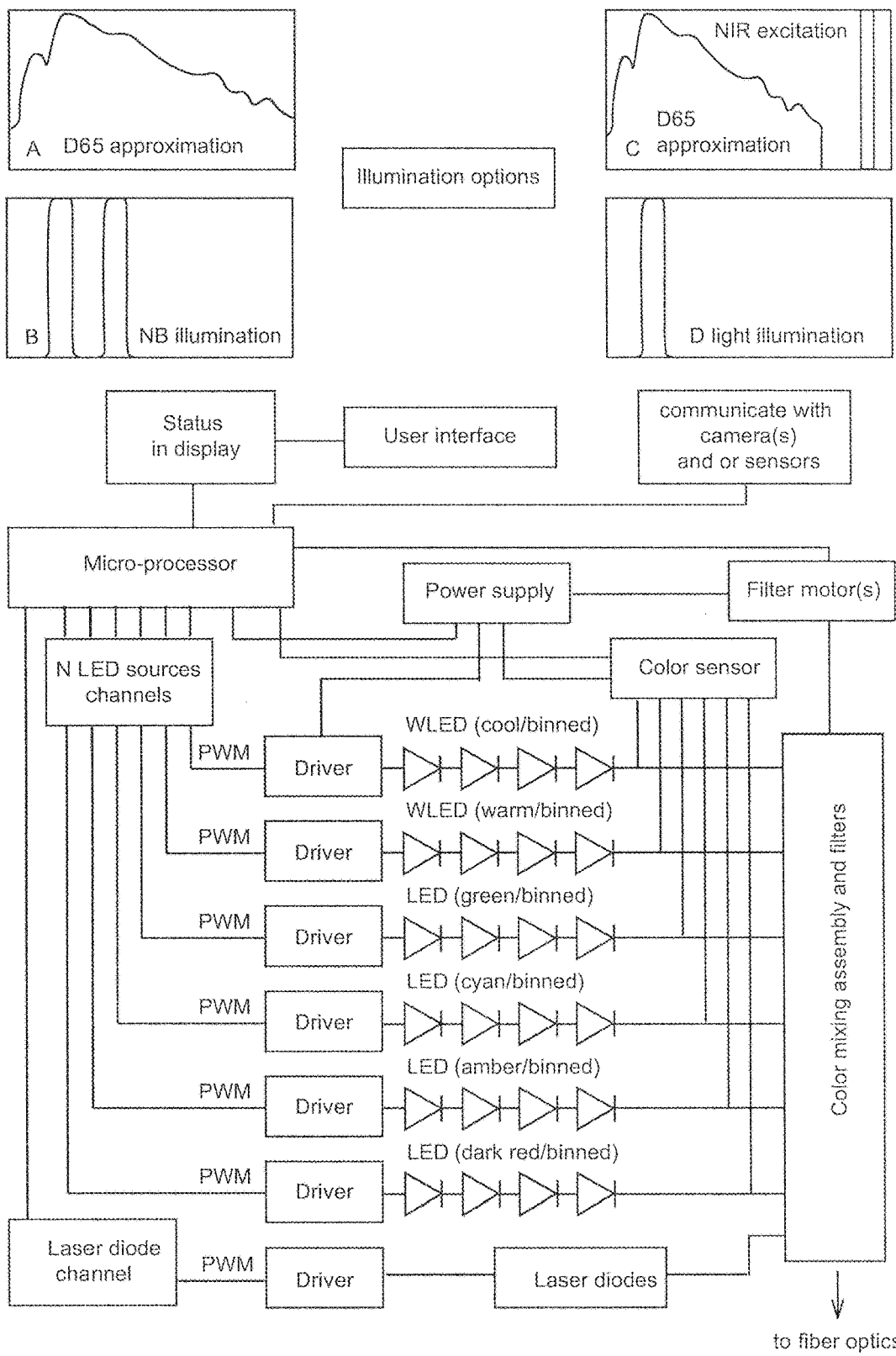
FIG. 2A is a block diagram of an example light source comprising a plurality of LEDs including, e.g., white light LEDs, and color LEDs, as well as laser diodes.

FIG. 2A is a block diagram schematically illustrating an example light source or illumination device. The example light source or illumination device includes a plurality of sub-source channels or sub-assemblies configured to generate light, and a controller subsystem comprising a micro-processor and/or other electronics, a color sensor, a color mixing assembly and one or more filters, and one or more filter motors. The micro-processor and/or electronics is operatively coupled to the plurality of sub-sources or sub-assemblies configured to generate light, the color sensor, and the one or more filter motors. The output of the color mixing assembly and one or more filters may be operatively coupled to fiber optics.

Certain embodiments described herein can utilize one or more color sensors having a color scheme division of the spectrum. Examples of color scheme divisions include a red-green-blue (RGB) color scheme division, a cyan-magenta-yellow-black (CMYK) color scheme division, a hue-saturation-value (HSV) color scheme division, or another color scheme division of the useful spectrum. Each color sensor can have one or more portions that are responsive to flux from corresponding portions of the spectrum (e.g., from green or cyan), or one or more portions that are responsive to one or more corresponding colored LEDs or groupings of LEDs. The color sensor can be configured to receive a portion of the total flux from the at least one optical emitter. For example, a portion of the mixing assembly (e.g., waveguide; mixing rod) can use total internal reflection to move flux in a direction from the light source to the output and a portion of the surface of the mixing assembly can comprise a dichroic coating which passes one or more wavelengths of interest to a color sensor. This portion of the flux can be coupled directly to the color sensor (e.g., by contact; via a fiber optic assembly; via a waveguide or mixing rod) to allow the color sensor to sample the flux for its spectral properties. In certain embodiments, the output spectrum of the light source can be managed by sampling the subdivisions of the flux in the waveguide (e.g., mixing rod) and by adjusting the power supplied to one or more of the LEDs (e.g., via the microprocessor and user interface), for example, to adjust the spectral characteristics of the light based on the samples obtained using the wavelength specific or color sensors.

In the design shown in FIG. 2A, each sub-source of the plurality of sub-sources comprises at least one optical emitter (e.g., an LED or laser diode) and at least one pulse-width modulation (PWM) circuit operatively coupled to the at least one optical emitter and configured to respond to control signals from the micro-processor or other electronics to drive the at least one optical emitter that is responsive to signals from the PWM circuit. For example, the output of the LEDs (e.g., in lumens) can be controlled by a PWM circuit generating digital signals (e.g., having a number of bits, such as 4 bits, 8 bits, 10 bits, with larger numbers of bits providing finer gradations of intensity levels) and a serial interface configured to transmit the digital signals to the corresponding optical emitters.

Figure 2B:
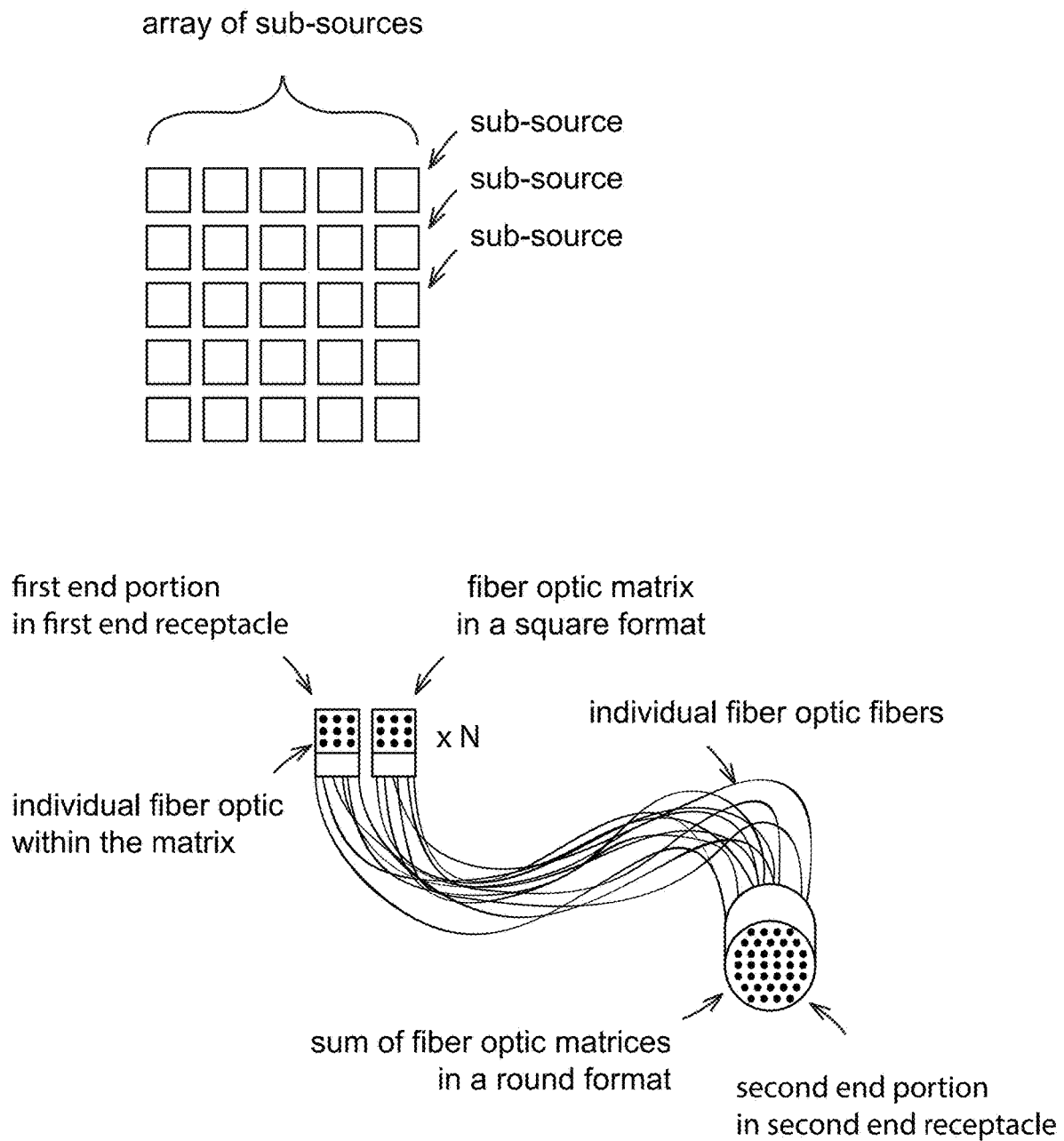
FIG. 2B schematically illustrates a portion of an example illumination device in accordance with certain embodiments described herein.

FIG. 2B schematically illustrates a portion of an example illumination device in accordance with certain embodiments described herein. The example illumination device shown in FIG. 2B comprises at least one sub-source (e.g., one or more pluralities of sub-sources, one or more arrays of sub-sources; one or more sub-source matrices) comprising one light emitter or a plurality of light emitters (e.g., LEDs) configured to produce light flux. The example illumination device further comprises a plurality of optical fibers (e.g., a fiber matrix). The different (e.g. each) optical fibers of the plurality of optical fibers may comprise a first end portion configured to receive the light flux from a corresponding light emitter or from a plurality of light emitters and a second end portion configured to emit the received light flux. The one or more light emitters are arranged in a first pattern. The first end portions may be arranged in the first pattern. and/or the second end portions may be arranged in a second pattern different from the first pattern.

For example, the at least one sub-source schematically illustrated in FIG. 2B comprises an array of square sub-sources. The light emitters of the array of square sub-sources are arranged in a first pattern (e.g., the array of sub-sources arranged in a rectilinear, square, or rectangular sub-pattern, and the light emitters of different sub-sources (e.g. each sub-source) also arranged in a rectilinear, square, or rectangular sub-pattern). The plurality of first end portions can be arranged in the same first pattern. The plurality of second end portions can be arranged in a different second pattern (e.g., a circular pattern; a second rectilinear pattern different from the first rectilinear pattern).

The plurality of optical fibers can be mechanically coupled together (e.g., contained in a matrix of adhesive such as epoxy or fused by temperature) in at least one first end assembly (e.g., at least one input receptacle) containing the first end portions and at least one second end assembly (e.g., at least one output receptacle) containing the second end portions. For example, as schematically illustrated by FIG. 2B, the at least one first end assembly can comprise a fiber optic matrix in a non-round (e.g., square; rectangular) format and the at least one second end assembly can comprise a sum of fiber optic matrices in a non-square format (e.g., round format). Likewise, the at least one first end assembly can comprise a fiber optic matrix in a non-round format and the at least one second end assembly can comprise a sum of fiber optic matrices in a different non-round format. The number of first end assemblies can be greater than the number of second end assemblies. For example, the number of first end assemblies can be 4, 9, 16, 25, 36, 49, or $N^2$ (e.g., each having a square format and configured to be in optical communication with a 2×2, 3×3, 4×4, 5×5, 6×6, 7×7, or N×N square array of square LEDs, respectively) and the number of second end assemblies can be 1, 2, 4, 6, 8, or less than $N^2$ (e.g., each having a circular format). Other examples can utilize non-square numbers (e.g., M×N, with M not equal to N, arranged in a rectangular format or other formats).

In certain embodiments, a first set of the first end portions can be in optical communication with the light emitters of a first sub-source and a second set of the first end portions can be in optical communication with the light emitters of one or more other sub-sources (e.g., a second sub-source; a third sub-source; N sub-sources). For example, a first set of the first end portions in a square end assembly and a second set of the first end portions in a different square end assembly can receive the light flux from the respective light emitters, and the second end portions of these optical fibers can be gathered into one or more circular end assemblies (e.g., to facilitate mixing of the received light flux from the respective light emitters). Such mixing may be accomplished, for example, by having the relative locations and/or order of different fibers in the first set of the first end portions be different from the relative locations and/or order of those same fibers in the second set of the first end portions In certain such embodiments, combining the light flux from various sub-sources (e.g., having differing color spectrums, power spectral densities, etc.) at the first end portions of the first end assemblies to be emitted from the second end portions of the second end assemblies which may have different arrangement and/or order, advantageously increases randomization of the flux output.

The plurality of optical fibers can be flexible (e.g., configured to be moved such that the second end portions are positioned at various selected locations relative to the first end portions). For example, the flexible plurality of optical fibers can be configured to allow the first end portions to be coupled to (e.g., adjacent to) the plurality of sub-sources (e.g., such that each first end portion is in optical communication with a corresponding one or more of the light emitters of a sub-source) and the second end portions to be coupled to (e.g., adjacent to) a filter assembly, lens assembly, mixer assembly, or an assembly combining any combination of filters, lenses and/or mixers (e.g., such that each second end portion is in optical communication with a corresponding portion of the filter or lens assembly, as described herein). For example, the individual optical fibers making up the fiber matrix can each have an outer diameter or lateral dimension selected to provide a desired flexibility (e.g., an outer diameter or lateral dimension of 20 microns, 30 microns, 50 microns, 70 microns, 80 microns, or in any range formed by any of these values). In certain other embodiments, the plurality of optical fibers can be fixed and the at least one sub-source can be configured to move, such that light emitters of a selected one or more sub-sources of the at least one sub-source are placed in optical communication with at least one selected set of optical fibers.

In certain embodiments, the sum of the areas of the sub-sources (e.g., areas of the input square formats) is substantially equal to the area of the output (e.g., circular output format) that is in optical communication with the sub-sources. In certain other embodiments, the first end portions of the individual optical fibers can be tapered (e.g., such that the numerical aperture of the fiber matrix is greater than or less than the input face of the fiber optic matrix).

In some implementations, the plurality of optical fibers could be heated and drawn producing a taper and/or tapers that could be combined together. In some implementations, the tapers could be different from one another and combined. The numerical aperture (NA) of a fiber may change as the area of the fiber changes. According, by tapering a fiber and producing a smaller diameter or cross-sectional area, the numerical aperture at that end can be caused to be increased. Decreasing the area of the second end portion, for example, may increase the numerical aperture of the second end portion and thus may increase the output angle or divergence angle of light exiting the optical fiber at the second end portion. Alternatively, one could orient the taper the other way. The first end portion of the fiber may be tapered to produce a smaller diameter or cross-sectional area at the first end compared to the first end portion. Consequently, the numerical aperture at the first end portion can be caused to be increased relative to the second end portion. The first end portion can thus accept more light from an LED by using the smaller end at the source and using the larger end where light may be output to focusing, collimating and/or mixing optics. Tapering and reducing the cross-section fiber at the input (e.g., reducing the cross-sectional area at the first end portion compared to the second end portion) can be used to capture more illumination or at the output (e.g., reducing the cross-sectional area at the second end portion compared to the first end portion) can be used to match the acceptance angle of an optical system, thereby improving efficiency.

Having different shaped formats for the first and second end assemblies can be useful in some instances to address the shape of structures in which emitters are packages. Emitters such as light emitting diodes (LEDs) may be included in square shaped LED sources such as LED arrays. As disclosed herein, a number of small LEDs can be optically coupled to a plurality of fiber matrices having square shape and then transmitted some distance from the emitters to a surgical device or transmitted internally within a surgical device. Light from the emitters may propagate through the fibers to one or more of the second end assemblies, which may be circular in some implementations as discussed herein. In some implementations, the number of second end assemblies including the second end portions is less than the number first end portions of fiber, which may be disposed proximal to the emitters. For example, one could have a 5×5 array of LED's coupled with one or more square fiber matrices and then gather these 25 fibers together into 1, 2, 3, 4, etc. circular second assemblies.

Systems, devices, and apparatus disclosed herein may be used to distribute light from one or more first end assemblies into a plurality of second end assemblies such as circular assemblies. Such systems, devices, and apparatus may be configured to directing light into focusing optics having a smaller diameter than the aggregate area of the emitters from which light originates. For example, the coupling fibers can permit coupling the optical power of a large LED or LED array into a plurality (e.g., 2, 3, 4, etc.) of focusing optic assemblies that individually have smaller areas than the larger LED or LED array. Similarly, the coupling fibers can permit coupling the optical power of one or more first end assemblies into a plurality (e.g., 2, 3, 4, etc.) of second end assemblies individually having smaller areas than the total cross-sectional area of the one or more first end assemblies.

In certain embodiments, sub-sources (e.g., arrays of sub-sources) can be configured to be moved individually or as a group to select at least one sub-source (e.g., at least one array of sub-sources) to be in optical communication with the plurality of first end portions in the at least one first end receptacle. For example, the sub-sources can be mounted on a support configured to move (e.g., rotate about a hub as the center of rotation; slide along a track), with the support configured to be positioned to place at least one sub-source (e.g., an array of sub-sources) in optical communication with the plurality of first end portions. Different sub-sources on the support can have characteristics that are different from the characteristics of the other sub-sources (e.g., one array of sub-sources can comprise light emitters with phosphors to emit white light; another array of sub-sources can comprise light emitters having a different color spectrum, power spectral density, etc.). These sub-sources (e.g., arrays of sub-sources) can be at different positions on the support (e.g., four arrays of sub-sources at the "12 o'clock," "3 o'clock," "6 o'clock," and "9 o'clock" positions of a rotating support), and the support can be positioned to place the array(s) having the desired characteristics (e.g., color spectrum) in optical communication with the plurality of first end portions. In certain other embodiments, the plurality of optical fibers can be fixed and the sub-sources (e.g., arrays of sub-sources) can be configured to be moved as a group to select at least one sub-source (e.g., at least one array of sub-sources) to be in optical communication with the plurality of first end portions in the at least one first end receptacle.

In certain embodiments, the portion of the illumination device advantageously allows the packing fraction of the optical fibers to be dimensionally less than the spacing of sub-sources. In some cases, the spacing of illumination devises or emitters can be impacted by thermal management considerations.

In some implementations, the light emitters are generally small and can be moved while the fiber optic matrix remains stationary and provides the light flux to additional optical systems or sub-systems (e.g., collimating assembly, mixing assembly, or focusing lens assembly or combinations thereof). In certain embodiments, the portion of the illumination device advantageously provides light flux from a square or rectangular array of sub-sources to optical systems or sub-systems that have different geometries (e.g., systems having a circular aperture or cross-section or field of view and/or that possibly see or transmit an image circle or light bundle).

The illumination device may comprise an illuminator that may be mounted on a stand or attached to different fixtures such as supports. The illumination device can be brought near the patient possibly to supplement overhead surgical lighting (e.g., used by the physician sans optical devices or with non-illuminated magnification devices, such as loupes, or to supplement other medical imaging modalities such as endoscopes, exoscopes, or cameras providing surgical microscope views). In addition or alternatively, the illumination device may be integrated with other medical imaging devices such as cameras providing surgical microscope views, etc.)

A range of advantages may be obtained using designs and configurations disclosed herein. For example, designs disclosed herein may facilitate mixing of light from LEDs that having different color that are selectively activated to provide a desired spectrum. Certain color lights may be added using selectively activated color emitters (e.g., LEDs) to supplement an otherwise discontinuous spectrum of white phosphor LEDs.

Additionally, a plurality of smaller emitters (e.g., LEDs) with gaps between them may have less thermal load than a single larger emitter (e.g., LED). Systems, devices, and apparatus disclosed herein may be used to combine light from such a plurality of smaller emitters. Systems, devices, and apparatus disclosed herein may be configured to direct light into smaller diameter focusing optics. Coupling fibers for example can permit coupling the power of a large LED into four smaller focusing optics.

A wide range of variations in the illumination device are possible. For example, the shapes and arrangements of the array of sub-sources as well as fiber optic matrix may be different. For example, shapes different from those disclosed for each of the components are possible. Likewise shapes other than square, rectangular, circular are possible. Additionally, although movement of the emitters has been described above, in some implementations the fiber may be moved. For example, the first end portions (e.g., the first end assembly) can be moved with respect to the emitters, sub-sources, and or second end portion in the second end assembly. Also, one or both of the first and second end assemblies can merely comprise fused fibers and does not include any extra components attached to the fibers. Additionally, any systems, devices, components, and/or features described herein can be combined with any other systems, devices, components, and/or features described herein. For example, any systems, devices, components, and/or features described in connection with FIG. 2B can be combined with any other systems, devices, components, and/or features described elsewhere herein, including with respect to any of the other Figures.

In certain embodiments, the at least one PWM circuit can be used to control the optical emitters to provide flicker-free illumination. Time-variant light artifacts (TLAs), commonly called fluctuations or flicker, are noticeable to most humans at frequencies below 70 Hz. Some people are sensitive in their central vision region to TLAs with frequencies up to 100 Hz, while using peripheral vision, TLAs can be perceived with frequencies up to 200 Hz. For wide field of view imaging systems, it is desirable to manage the illumination to improve (e.g., optimize) "time variant light quality," especially since such wide field of view imaging systems engage the peripheral vision of the user. By comparison, endoscopic images viewed through ocular systems have narrow apparent fields of view (e.g., 10 to 30 degrees). Viewing a medical image on a monitoring screen in 2D or 3D (e.g., attached to an arm and surgical stand) may well engage fields of view of 30 to 45 degrees. A surgical microscope or electronic near eye display (e.g., fixed on an arm or worn) can have an apparent field of view of 60 to 90 degrees, and immersive displays (e.g., head mounted or fixed on an arm) can engage nearly the entire periphery of a user's vision system. Thus, in certain embodiments described herein the illumination system utilizes the at least one PWM circuit to control the generated light to conform to user requirements for perceptually flicker free illumination (e.g., substantially above 200 Hz). For example, the at least one PWM circuit can be configured to control the generated light to direct light onto the optical emitters at a pulse rate sufficiently fast to avoid detection of flicker by the user, in one or both of the user's central viewing region and the user's peripheral viewing region.

In certain embodiments, the at least one PWM circuit can be used to compensate for differences between the color characteristics of different medical cameras. For example, single-chip medical cameras and three-chip medical cameras have different color characteristics due to their color separation filtering. In some cases, for example, single-chip cameras can use a Bayer filter arrangement with different color filters over different pixels in a repeating pattern, while three-chip cameras can use three dichroic filters arranged to produce three different color channels (e.g., a red, green, or blue channel) each with its own sensor array. The pixels in these sensor arrays used in a three-chip camera have their respective color channels that are sensitive primarily in different respective portion of the spectrum (e.g., red, green, blue, etc.) though there can be spectral or wavelength overlap among the different sensor arrays. The output in color space of these two families of cameras can produce slightly different responses. Additionally, medical cameras from different manufacturers may use different sensor arrays which can add to the differences. Using the at least one PWM circuit to compensate for differences between different sensor arrays having different spectral characteristics or spectral responsivities. For example, using the at least one PWM circuit to compensate for differences between the color characteristics of these different medical cameras can advantageously allow better color matching between single-chip sensors and three-chip sensors and between the products from different camera manufacturers. The modulation circuitry can modulate the at least one light source (e.g. at least one LED) differently for different sensor arrays or cameras.

Various optical emitters can be configured to output illumination having one or more characteristics (e.g., intensity, wavelength, etc.). For example, some optical emitters can be configured to output optical power that has a spectral distribution similar to a CIE standard Illuminant D65. The characteristics of the light output from an optical emitter can be configured to match the detection capabilities of the various cameras that are configured to view the illumination output from the optical emitter. The optical emitter can be configured to adjust the characteristics of the light output (e.g., using the modulation circuitry) to more closely match the detection capabilities of the camera/sensor viewing the illumination output from the optical emitter. For example, the optical emitter can comprise a look up table of settings that includes the illumination characteristics that more closely match the various cameras/sensors that can view illumination output from the optical emitter. Various cameras/sensors can identify themselves over a communication link or bus, and the optical emitter can adjust the characteristics of the light output to more closely match the detection capabilities of the identified cameras/sensors. This feature can be advantageous when one or more cameras/sensors are switched on or off or are switched from being used to present images to not being used to present images or vice versa.

In certain embodiments, the at least one PWM circuit can be used to control the optical emitters to conform to various regulations regarding their use. For example, illumination is a time-based quantity, and the production of heat in tissue caused by the illumination is also a time-based quantity. For another example, the optical emitters can comprise one or more laser diodes (e.g., for excitation of an exogeneous dye), in which case the illumination source may potentially be subject to compliance with various regulatory requirements.

As shown in FIG. 2A, the example illumination device comprises N LEDs sub-source channels and a laser diode sub-source channel. One or more LED sub-source channels and in some cases each LED sub-source channel may comprise a PWM circuit and a plurality of corresponding LEDs operatively coupled to the corresponding PWM circuit, and the laser diode sub-source channel comprises a PWM circuit and one or more laser diodes operatively coupled to the corresponding PWM circuit. The PWM circuits are operatively coupled to the power supply. For example, as shown in FIG. 2A, six LED sub-source channels each have a corresponding PWM circuit and a corresponding set of LEDs, with each LED sub-source channel generating light in a corresponding spectrum: WLED (cool/binned), WLED (warm/binned), LED (green/binned), LED (cyan/binned), LED (amber/binned), and LED (dark red/binned). As used herein, "binned" refers to a collection of optical emitters (e.g., LEDs) with one or more similar properties and that are grouped together. The bins or groups can be defined by one or more properties including but not limited to, intensity distribution plots, lumen output, color temperature, and voltage. For example, a collection of LEDs with similar lumen output, but slightly different color temperatures within the green range can be binned together in a LED sub-source channel. Using bins can be advantageous by widening the peak distribution of the spectral peak of the light generated by the LED sub-source channel (e.g., for LEDs having individual colors, such as red, green, blue, amber, cyan, etc., and for white light LEDs). Each of the N LED sub-source channels also comprises one or more corresponding color sensors which are operatively coupled to the power supply and to the output of the corresponding optical emitters of the channel.

Optical signals outputted from the optical emitters are transmitted to a color mixing assembly and filters configured to generate light having a corresponding spectrum and to provide this light to the fiber optics.

In the example light source shown in FIG. 2A, in a seventh sub-source channel, a plurality of laser diodes are controlled by digital signals received from a corresponding PWM circuit, and optical signals outputted from the laser diodes are transmitted to the color mixing assembly and filters. Other numbers and combinations of sub-sources/sub-source channels and emitters are possible. Additionally, the illumination device may include additional components or may exclude one or more of the components shown and/or the arrangement of components may be different. Other features may be varied as well.

The light from the outputs of the plurality of sub-sources is directed to the one or more filters inputted into the color mixing assembly. For example, the plurality of sub-sources can generate corresponding light beams, the light beams can be transmitted through corresponding filters of the one or more filters to the color mixing assembly. In some cases, the color mixing assembly combines the light beams into a single composite beam. In some cases, the color mixing assembly can comprise at least one collimator configured to collimate the light beams to a single composite light beam. In certain designs, the light source further comprises an optical focusing assembly to converge the composite light beam and to transmit the composite light beam to a receiving fiber optic conduit or cable.

The color sensor can be operatively coupled to the outputs of the plurality of sub-sources (e.g., the N LED sources channels; the laser diode channel) and can be configured to detect and report on the spectral properties of the outputs of the individual sub-sources and on the overall output to possibly be recorded, controlled, and displayed. Information generated by the color sensor can be provided to the microprocessor, which in response, can transmit control signals to the optical emitters of the plurality of sub-sources and the one or more filter motors. For example, the color sensor can comprise one or more power output sensors configured to detect the output of one or more output channels (e.g., one or more of the N LED sources channels and the laser diode channel) and can be operatively coupled to the microprocessor or other electronics (e.g., as shown in FIG. 2A) to provide feedback signals indicative of one or more characteristics of the detected light (e.g., output intensity at the excitation peak of the laser diodes). The micro-processor can be configured to be responsive to the feedback signals by controlling the one or more output channels. In some designs, the illumination device or system can be configured to provide one or more modes the yield illumination having desired spectral characteristics. In some cases, the illumination device or system includes a user interface through which the user can select between a plurality of such modes.

FIGS. 3-6 schematically illustrate example illumination modes which can be offered to the user in a user interface which communicates with one or more displays and one or more cameras.

Figure 3:
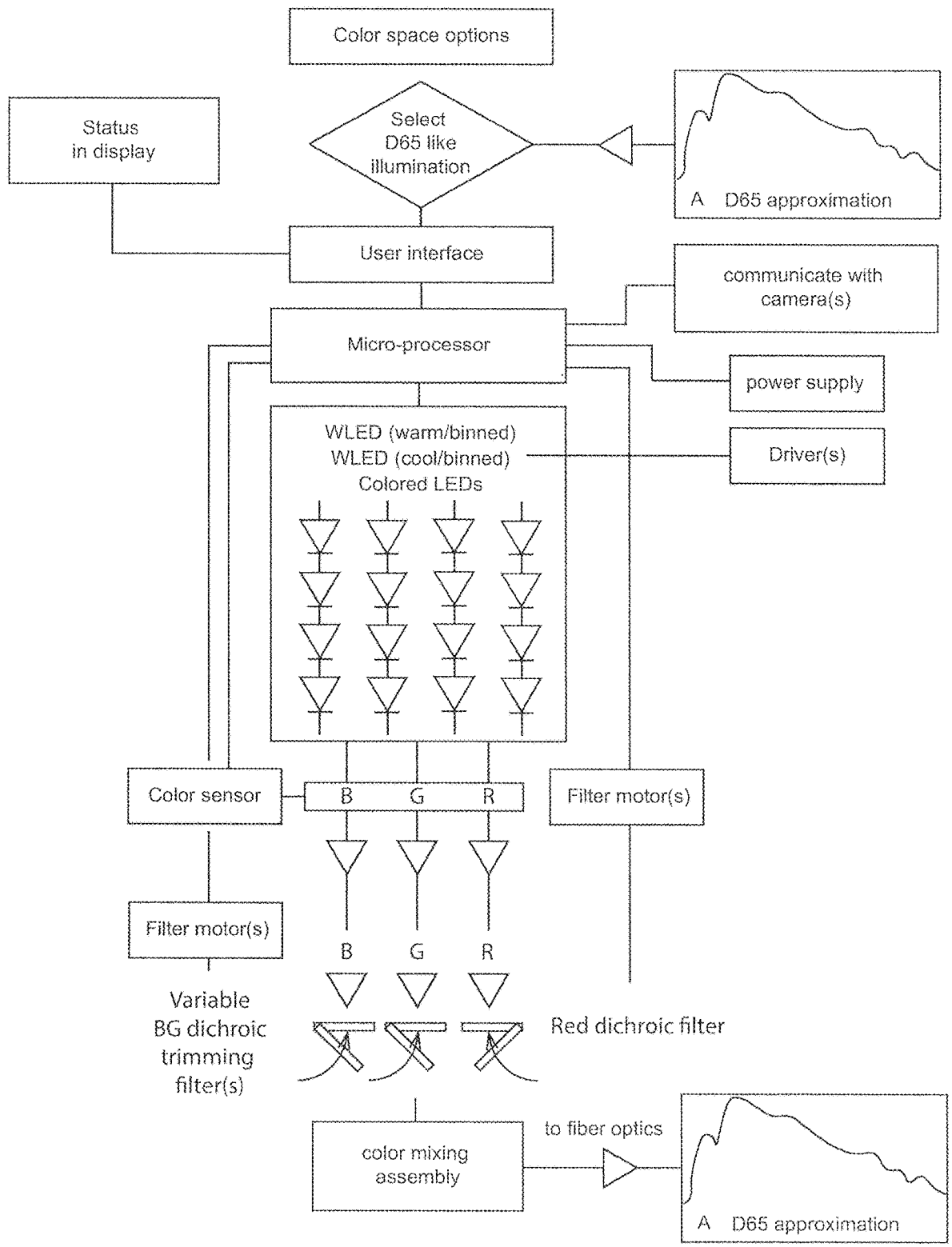
FIGS. 3-6 schematically illustrate example illumination modes that can be offered to the user, for example, via a user interface. Such a user interface may communicate, for example, with one or more displays and one or more cameras.

FIG. 3 illustrates an example Mode A that provides an illumination output that approximates CIE illuminant D65, and that approximates the illumination output of a xenon lamp. In addition, by adjusting power and filter configurations of the example light source, different color balances can be achieved. As illustrated, the illumination system includes blue green dichroic filters and red dichroic filters that having spectral characteristics that can be gradually tuned by varying the orientation of the filter with respect the incident light beams. In addition to the blue green dichroic filters and red dichroic filters, a band stop filter can be used to extinguish the red channel.

Figure 4:
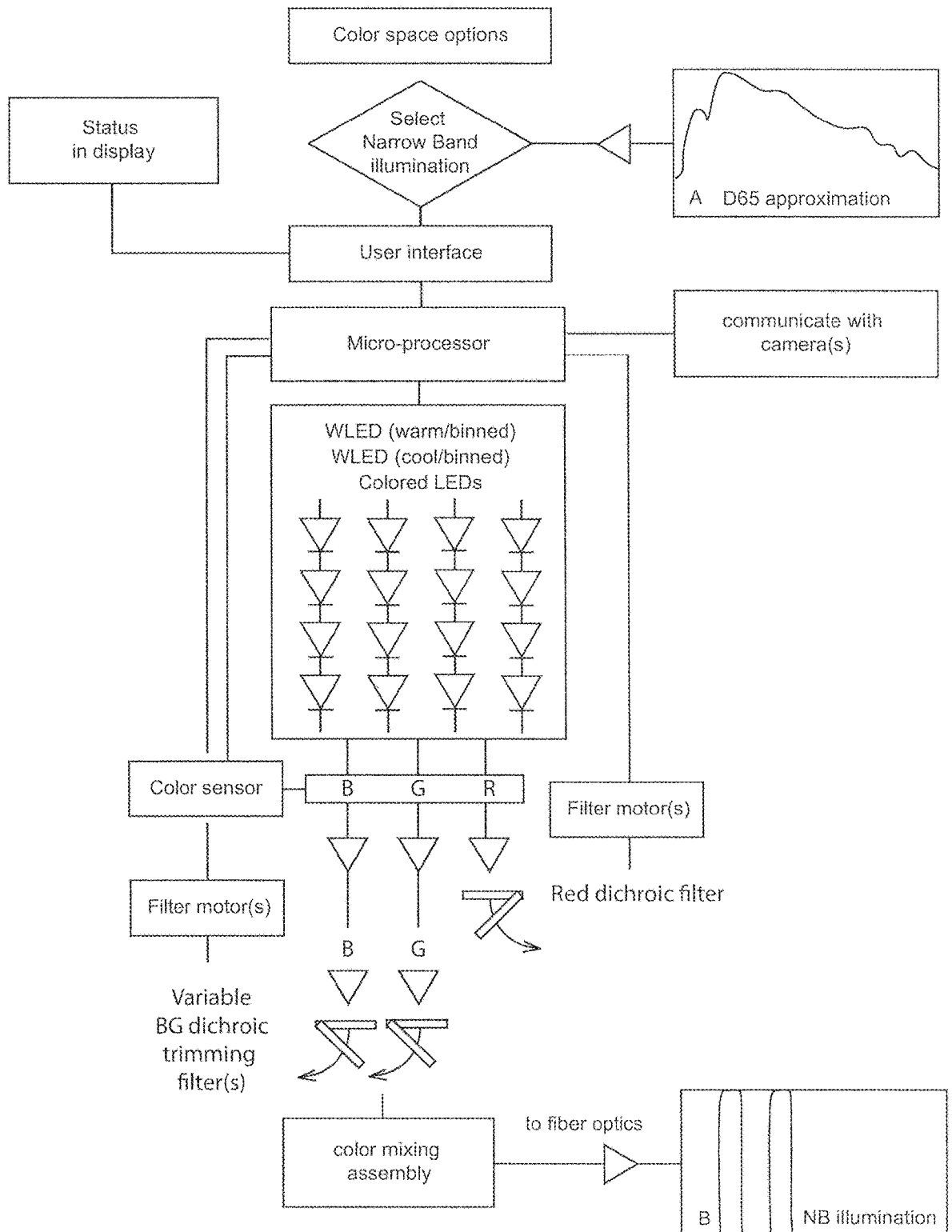

FIG. 4 illustrates an example Mode B that provides an illumination output that approximates an illumination output for narrow-band imaging (NBI). For example, the wavelength range for NBI can comprise one or more of the following: blue waveband (e.g., 440 nm-460 nm; range centered at 415 nm and having width of about 10 nm, 20 nm, or 30 nm; range having width greater than 10 nm, greater than 20 nm, greater than 30 nm, less than 10 nm, less than 20 nm, less than 30 nm); green waveband (e.g., 540 nm-560 nm; range centered at 540 nm and having width of about 10 nm, 20 nm, or 30 nm; range having width greater than 10 nm, greater than 20 nm, greater than 30 nm, less than 10 nm, less than 20 nm, less than 30 nm). In addition, the illumination output can advantageously be transitioned from visual imaging to NBI under the user's control. As illustrated, the illumination system includes blue green dichroic filters and red dichroic filters that having spectral characteristics that can be gradually tuned by varying the orientation of the filter with respect the incident light beams. In addition to the blue green dichroic filters and red dichroic filters, a band stop filter can be used to extinguish the red channel.

Figure 5:
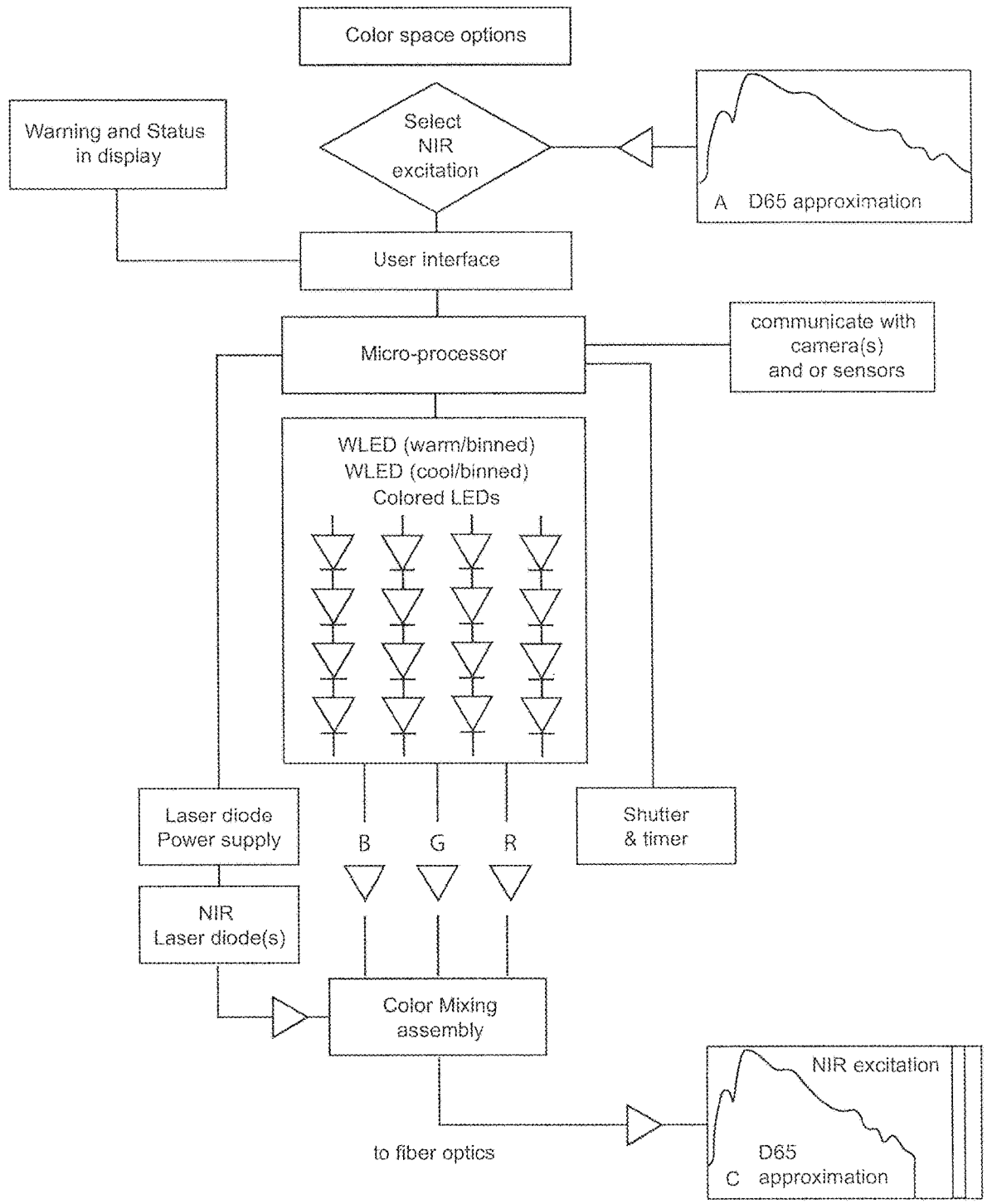

FIG. 5 illustrates an example Mode C which provides an illumination output which approximates CIE illuminant D65 plus NIR excitation.

Figure 6:
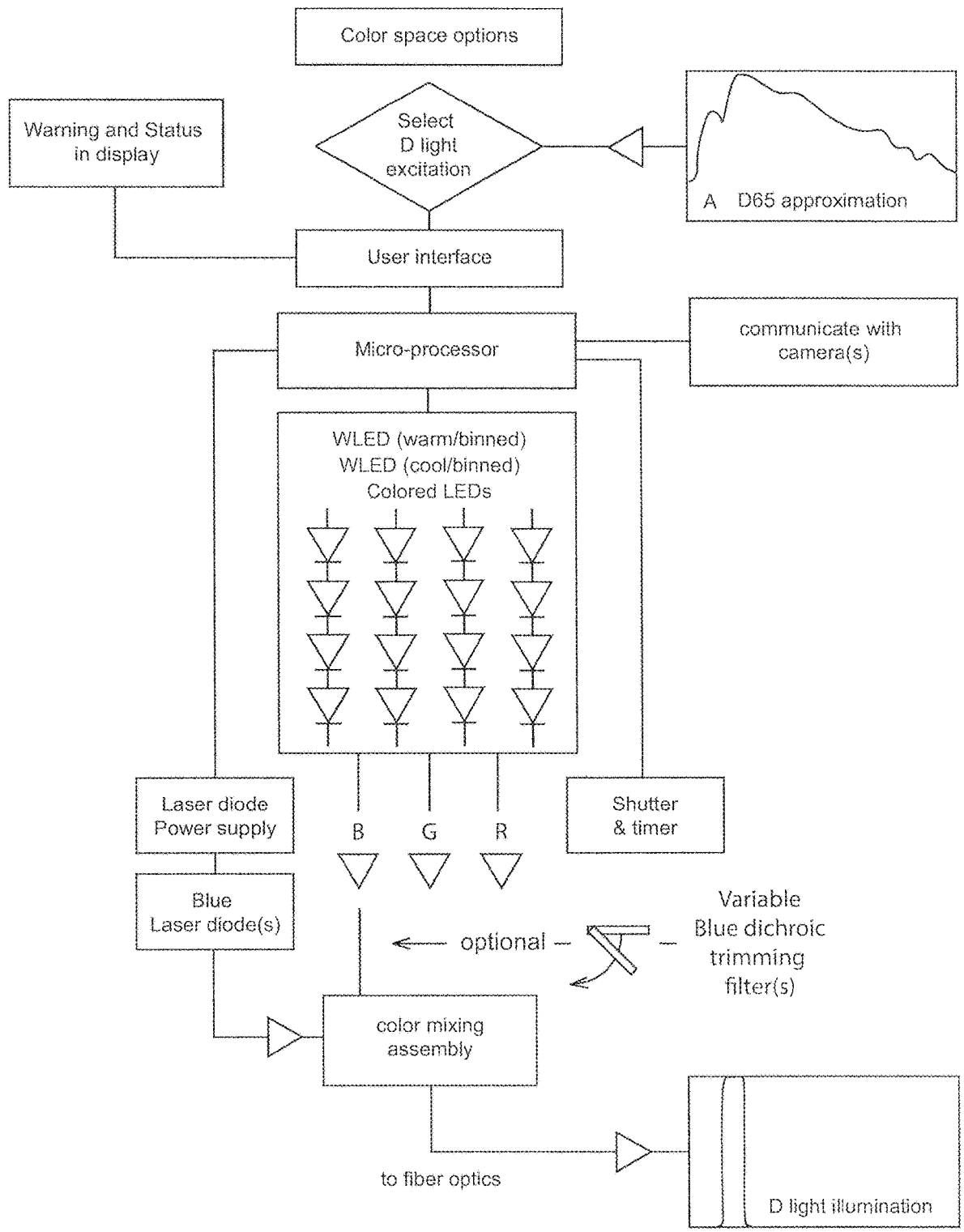

FIG. 6 illustrates an example Mode D that provides an illumination output that approximates a blue light only. For example, the Mode D light can comprise a narrow band of blue light (e.g., short wavelength blue light, preferentially absorbed at the tissue surface; approximately one-half of the blue waveband component of NBI; 440 nm-450 nm; 450 nm-460 nm). As another example, the Mode D light can comprise blue illumination as used in photodynamic diagnosis (PDD) of lesions (e.g., flat lesions; epithelial lesions; carcinomas), e.g., in cystoscopy, urology, gynecology, gastroenterology.

In one example, Mode A as shown in FIG. 3 can be selected by the user, and the following example sequence of actions can be performed by the example light source shown in FIG. 2A:

Initiate current to a color sensor with driver currents to the LEDs off, setting the black point (e.g., zero RGB values).

Initiate current to an array of warm and cool white LEDs.

Use color sensor to measure luminance value Y in beam path proximal to fiber optic cable at maximum drive current. Dimming can be a percentage of this value, for example, a lesser value may be used for maximum to account for lifetime changes, and Mode B can utilize a driver current that is raised from that of Mode A.

Read value and store.

Assign warm LED to red-difference chroma components of the color space (CR) in color sensor, read and store value.

Assign warm LED to blue-difference chroma components of the color space (CB) in color sensor, read and store value.

Compute color values of color space for nominal position (setting white balance) according to RGB values in matrix to find white point. Read and store values.

Measure RGB values in CIE xyY space. These values can be derived by integrating the CIE color matching functions with the measurements of spectral power distribution.

Initiate current to an array of colored LEDs (Cyan, Green, Amber, Deep Red, etc.) (each discrete LED color is given a PWM channel to control driver current).

Remeasure RGB values in CIE xyY space.

Compare resulting CIE xy values with D65 in LUT (look up table).

Raise or lower colored LED channel driver current to approximate D65 as stored in LUT.

Results in nominal balanced white light configuration, Mode A.

Report color sensor values to user interface for display or storage.

In another example, Mode B as shown in FIG. 4 can be selected by the user for narrow-band imaging, and the following example sequence of actions can be performed by the example light source shown in FIG. 2A:

Use Mode A for starting point.

Apply current to red filter motor, which tilts the red dichroic filter in the warm and cool white LED beam paths, thereby reducing the red light output. Optionally, an iris diaphragm, band stop filter, and/or neutral density filter (e.g., a rotationally variable neutral density filter, variable in steps or continuously variable) can be used to control the red light channel originating from white light LEDs, which would utilize a different physical layout.

Simultaneously apply additional current to the warm and cool white LED PWM driver channels, thereby raising light output in the remaining blue and green beam paths.

Simultaneously apply additional current to the cyan and green LED PWM driver channels, thereby raising light output in the blue and green beam paths. In certain embodiments, violet and blue could be added as well.

Initiate current to tilting a blue green trimming filter motor which tilts the filter in the beam path and sharpens cut-off and cut-on blue and green wavebands.

Optionally, raise or lower current to LEDs drivers to raise or lower the blue and green output independently. In certain embodiments, violet and blue could be added as well.

Report color sensor values to user interface for display or storage.

In another example, Mode C (e.g., which can be available as an additional modality to either Mode A or B), as shown in FIG. 5, can be selected by the user for NIR excitation added to D65-like illumination of Mode A, and the following example sequence of actions can be performed by the example light source in FIG. 2A:

Select in response to the user interface either the NIR laser diode or the NIR laser diode options.

Display warnings for eye safety in display.

Apply current to NIR laser diode or select from NIR laser diode options to initiate.

Communicate to the one or more cameras that NIR excitation energy is to be used and what type (e.g., 700 nm type or 808 nm ICG type) source is to be initiated. In certain cases, the one or more cameras will have modes or filters for source type (e.g. excitation blocking filters).

Report output value, in radiant flux or current, and source type to user interface and display.

In another example, Mode D, as shown in FIG. 6, can be selected by the user for short blue light for photodynamic therapy (e.g., using photosensitizing agent excitation), where the excitation waveband is in the deep blue and emission in the 625-700 nm range, and the following example sequence of actions can be performed by the example light source in FIG. 2A:

Select in response to the user interface either the blue laser diode or the blue laser diode options (e.g., excitation sources in the 405 nm range).

Display warnings for eye safety in display.

Apply current to the blue laser diode or select from the blue laser diode options to initiate.

Communicate to the one or more cameras that the blue excitation energy is to be used and what type (e.g., 405 nm or Sorel type with Q range options) source is to be initiated. In certain cases, the one or more cameras will have modes or filters for source type (e.g., shutter and timing communication between illuminator and camera).

Report output value, in radiant flux or current, and source type to user interface and display.

The controller subsystem can be configured to allow the user to choose one or more modes or combinations of modes, including those shown in FIGS. 3-6 as well as other modes. For example, NIR excitation could be added to the NBI of Mode B or to Mode D. Likewise, the controller subsystem can comprise one or more transition filters which may allow the user to selectively switch among one or more modes, including those shown in FIGS. 3-6 as well as other modes. For example, the micro-processor and one or more filters of the controller subsystem can be configured to allow the user to controllably fade the illumination output from Mode A to Mode D and back.

FIGS. 3-6 also schematically illustrate examples with one or more filters that can be tuned to gradually change the spectral characteristic of the light after interacting with the tunable filter. As discussed above, various filters may comprise one or more stacks of (e.g., dielectric) layers, which may act in a band pass manner by optical interference, rather than absorption, to shift and/or attenuate the spectral power distribution. Certain examples described herein advantageously allow the light source to illuminate various biologically important features of the patient by varying the positioning of the filters through angle space so that the incident angle of light in the illuminator changes with respect to the filter stack. The dielectric stack can be a periodic layering of materials with high index of refraction, such as titanium dioxide (n=2.4) or zinc sulfide (n=2.32), and low index materials, such as magnesium fluoride (n=1.38). The physical thickness of these material layers can be configured to produce a predetermined optical path difference due to the differing indices. Alternately, ordered layers with high, low and medium index materials can be utilized to both pass desired wavebands and attenuate other wavebands and/or to shift the central wavelength (CWL) region to shorter wavebands. In certain embodiments, the filters are tilted through prescribed angles in a collimated beam.

Any systems, devices, components, and/or features described herein can be combined with any other systems, devices, components, and/or features described herein. For example, any systems, devices, components, and/or features described in connection with FIG. 2B can be combined with any other systems, devices, components, and/or features described elsewhere herein, including with respect to any of the other Figures. Various examples of illumination devices and their methods of use are described herein, such as the examples enumerated below:

Example 1

An illumination device comprising:
a plurality of sub-sources, each sub-source configured to generate a light beam;
at least one filter configured to controllably adjust a spectral power distribution of at least one of the light beams generated by a corresponding at least one sub-source of the plurality of sub-sources and incident on the at least one filter, the spectral power distribution controllably adjusted to provide a gradual transition or a variable change of the spectral power distribution; and
a color mixing assembly configured to receive the light beams from the at least one filter and to generate a composite light beam,
wherein the at least one filter has a spectral distribution that is altered when the at least one filter is tilted with respect to the light beam incident thereon or vice versa.

Example 2

The illumination device of Example 1, wherein at least one sub-source of the plurality of sub-sources comprises at least one solid-state semiconductor optical emitter producing monochromatic visible light when an electric current is provided.

Example 3

The illumination device of Example 1 or Example 2, wherein at least one sub-source of the plurality of sub-sources comprises at least one solid-state optical emitter containing phosphor and producing a white light output.

Example 4

The illumination device of any of Examples 1-3, wherein all the sub-sources comprise at least one colored LED.

Example 5

The illumination device of any of Examples 1-4, wherein all the sub-sources comprise at least one laser diode.

Example 6

The illumination device of any of Examples 1-5, wherein the at least one filter comprises an interference filter.

Example 7

The illumination device of any of Examples 1-6, wherein the at least one filter comprises at least one plane-parallel plate with one or both surfaces coated with a thin film coating stack comprising a plurality of layers with different indices of refraction, wherein tilting of the plate relative to the light beam transmitted through the plate selectively passes or blocks certain wavelength regions of the light beam.

Example 8

The illumination device of Example 7, wherein the at least one plate is positioned in a collimated beam path of the light beam.

Example 9

The illumination device of any of Examples 1-8, wherein at least one sub-source of the plurality of sub-sources comprises at least one optical emitter and at least one pulse-width modulation (PWM) circuit configured to control the at least one optical emitter to improve time variant light quality of the at least one sub-source.

Example 10

The illumination device of any of Examples 1-9, wherein at least one sub-source of the plurality of sub-sources comprises at least one optical emitter and at least one pulse-width modulation (PWM) circuit configured to control the at least one optical emitter to conform to user requirements for perceptually flicker free illumination.

Example 11

The illumination device of any of Examples 1-10, wherein at least one sub-source of the plurality of sub-sources comprises at least one optical emitter and at least one pulse-width modulation (PWM) circuit configured to control the at least one optical emitter to provide perceptually flicker free illumination at frequencies substantially above 200 Hz.

Example 12

The illumination device of any of Examples 1-11, wherein the color mixing assembly comprises a collimator.

Example 13

The illumination device of any of Examples 1-12, further comprising an optical focusing assembly to converge the composite light beam and to transmit the composite light beam to a receiving fiber optic conduit or cable.

Example 14

The illumination device of any of Examples 1-13, wherein the plurality of sub-sources comprises at least one sub-source comprising a plurality of light emitters configured to produce light flux, the illumination device further comprising a plurality of optical fibers, each optical fiber of the plurality of optical fibers comprising a first end portion configured to receive the light flux from a corresponding light emitter and a second end portion configured to emit the received light flux, the light emitters arranged in a first pattern, the first end portions arranged in the first pattern, and the second end portions are arranged in a second pattern different from the first pattern.

Example 15

An illumination device comprising:
  at least one sub-source comprising a plurality of light emitters configured to produce light flux; and
  a plurality of optical fibers, each optical fiber of the plurality of optical fibers comprising a first end portion configured to receive the light flux from a corresponding light emitter and a second end portion configured to emit the received light flux, the light emitters arranged in a first pattern, the first end portions arranged in the first pattern, and the second end portions are arranged in a second pattern different from the first pattern Example 16

The illumination device of Example 14 or Example 15, wherein the at least one sub-source comprises an array of sub-sources.

Example 17

The illumination device of any of Examples 14-16, wherein the array of sub-sources is arranged in a rectilinear, square, or rectangular first sub-pattern, the light emitters of each sub-source arranged in a rectilinear, square, or rectangular second sub-pattern, the first pattern comprising the first sub-pattern and the second sub-pattern, and the second end portions are arranged in a circular pattern.

Example 18

The illumination device of any of Examples 14-17, wherein the plurality of optical fibers are mechanically coupled together in at least one first end assembly containing the first end portions and at least one second end assembly containing the second end portions.

Example 19

The illumination device of Example 18, wherein the at least one first end assembly has a non-round format and the at least one second end assembly has a round format or a different non-round format.

Example 20

The illumination device of Example 18, wherein the at least one first end assembly has a square format and the at least one second end assembly has a round format.

Example 21

The illumination device of any of Examples 14-20, wherein the plurality of optical fibers are configured to be moved such that the second end portions are positioned at various selected locations relative to the first end portions.

Example 22

The illumination device of any of Examples 14-21, wherein the first end portions are tapered.

Example 23

The illumination device of any of Examples 14-16, wherein the plurality of optical fibers are mechanically coupled together in a plurality of end assemblies containing the first end portions and one second end assembly containing the second end portions.

Example 24

The illumination device of any of Examples 14-16, wherein the plurality of optical fibers are mechanically coupled together in a plurality of end assemblies containing the first end portions and a plurality of second end assemblies containing the second end portions.

Example 25

The illumination device of any of Examples 14-16, wherein the first end portions are tapered with respect to the second end portions such that the first end portions are smaller than the second end portions.

Example 26

The illumination device of any of Examples 14-16, wherein the second end portions are tapered with respect to the first end portions such that the second end portions are smaller than the first end portions.

Although described above in connection with particular embodiments, it should be understood the descriptions of the embodiments are illustrative and are not intended to be limiting. Various modifications and applications may occur to those skilled in the art without departing from the true spirit and scope of the invention.

What is claimed is:

1. An illumination device comprising:
   a plurality of sub-sources, each sub-source configured to generate light beams;
   at least one filter configured to controllably adjust a spectral power distribution of at least one of the light beams generated by a corresponding at least one sub-source of the plurality of sub-sources and incident on the at least one filter, the spectral power distribution controllably adjusted to provide a gradual transition or a variable change of the spectral power distribution; and
   a color mixing assembly configured to receive the light beams from the at least one filter and to generate a composite light beam,
   wherein the at least one filter has a spectral distribution that is altered when the at least one filter is tilted with respect to the light beam incident thereon or vice versa,
   wherein the plurality of sub-sources comprises at least one sub-source comprising a plurality of light emitters configured to produce light flux, the illumination device further comprising a plurality of optical fibers, each optical fiber of the plurality of optical fibers comprising a first end portion configured to receive the light flux from a corresponding light emitter and a second end portion configured to emit the received light flux, the light emitters arranged in a first pattern, the first end portions arranged in the first pattern, and the second end portions are arranged in a second pattern different from the first pattern.

2. The illumination device of claim 1, wherein the at least one sub-source of the plurality of sub-sources comprises at least one solid-state semiconductor optical emitter producing monochromatic visible light when an electric current is provided.

3. The illumination device of claim 1, wherein the at least one sub-source of the plurality of sub-sources comprises at least one solid-state optical emitter containing phosphor and producing a white light output.

4. The illumination device of claim 1, wherein all the sub-sources comprise at least one colored LED.

5. The illumination device of claim 1, wherein all the sub-sources comprise at least one laser diode.

6. The illumination device of claim 1, wherein the at least one filter comprises an interference filter.

7. The illumination device of claim 1, wherein the at least one filter comprises at least one plane-parallel plate with one or both surfaces coated with a thin film coating stack comprising a plurality of layers with different indices of refraction, wherein tilting of the plate relative to the light beam transmitted through the plate selectively passes or blocks certain wavelength regions of the light beam.

8. The illumination device of claim 7, wherein the at least one plate is positioned in a collimated beam path of the light beam.

9. The illumination device of claim 1, wherein the at least one sub-source of the plurality of sub-sources comprises at least one optical emitter and at least one pulse-width modulation (PWM) circuit configured to control the at least one optical emitter to improve time variant light quality of the at least one sub-source.

10. The illumination device of claim 1, wherein the at least one sub-source of the plurality of sub-sources comprises at least one optical emitter and at least one pulse-width modulation (PWM) circuit configured to control the at least one optical emitter to conform to user requirements for perceptually flicker free illumination.

11. The illumination device of claim 1, wherein the at least one sub-source of the plurality of sub-sources comprises at least one optical emitter and at least one pulse-width modulation (PWM) circuit configured to control the at least one optical emitter to provide perceptually flicker free illumination at frequencies substantially above 200 Hz.

12. The illumination device of claim 1, wherein the color mixing assembly comprises a collimator.

13. The illumination device of claim 1, further comprising an optical focusing assembly to converge the composite light beam and to transmit the composite light beam to a receiving fiber optic conduit or cable.

\* \* \* \* \*